US007967793B2

(12) United States Patent
Sibbitt, Jr. et al.

(10) Patent No.: US 7,967,793 B2
(45) Date of Patent: Jun. 28, 2011

(54) RECIPROCATING PROCEDURE SYRINGES

(75) Inventors: Wilmer L. Sibbitt, Jr., Albuquerque, NM (US); Randy R. Sibbitt, Helena, MT (US)

(73) Assignee: Avance Medical Devices, Inc., Albuquerque, NM (US)

( * ) Notice: Subject to any disclaimer, the term of this patent is extended or adjusted under 35 U.S.C. 154(b) by 1197 days.

(21) Appl. No.: 11/336,171

(22) Filed: Jan. 20, 2006

(65) Prior Publication Data
US 2006/0184130 A1 Aug. 17, 2006

Related U.S. Application Data

(60) Provisional application No. 60/646,190, filed on Jan. 21, 2005.

(51) Int. Cl.
*A61M 5/00* (2006.01)
(52) U.S. Cl. ...................................................... 604/191
(58) Field of Classification Search .................. 604/152, 604/181, 187, 191, 80–92, 35
See application file for complete search history.

(56) References Cited

U.S. PATENT DOCUMENTS

| 3,685,514 | A | 8/1972 | Cheney |
| 3,990,446 | A | 11/1976 | Taylor |
| 4,036,232 | A | 7/1977 | Genese |
| 4,437,859 | A | 3/1984 | Whitehouse |
| 4,471,765 | A | 9/1984 | Strauss |
| 4,484,915 | A | 11/1984 | Tartaglia |
| 4,594,073 | A | 6/1986 | Stine |
| 4,610,666 | A | 9/1986 | Pizzino |
| 4,619,272 | A | 10/1986 | Zambelli |
| 4,639,248 | A | 1/1987 | Schweblin |
| 4,967,762 | A | 11/1990 | DeVries |
| 5,115,816 | A | 5/1992 | Lee |
| 5,135,511 | A | 8/1992 | Houghton |

(Continued)

OTHER PUBLICATIONS

Hopper KD, Abendroth CS, Sturtz KW, Matthews YL, Shirk SJ: Fine-needle aspiration biopsy for cytopathologic analysis: utility of syringe handles, automated guns, and the nonsuction method. Radiology 1992;185:819-824.

(Continued)

*Primary Examiner* — Matthew F Desanto

(57) ABSTRACT

A reciprocating syringe that can be used in connection with existing syringe barrels and fittings. Some embodiments comprise a frame, adapted to retain two existing syringe barrels. The frame can accommodate fittings on one or both barrels. The invention also provides a plunger complex, comprising two plungers, each adapted for use with one of the syringe barrels. The two plungers are coupled such that pushing of each plunger into its barrel causes the other plunger to pull outwards relative to its barrel. The two plungers can be coupled by a flexible line attached to one plunger, routed from the plunger out of the corresponding barrel into the other barrel, and attached to the other plunger. The invention contemplates various frame configurations to accommodate desired line and pulley performance characteristics. Other embodiments comprise a frame adapted to retain an existing syringe barrel, and an auxiliary actuator mounted with the frame. Such an actuator can provide a syringe-like plunger operation, or can comprise other manipulable structures. The auxiliary actuator can be coupled to a plunger adapted for use with the syringe barrel, such that pushing the plunger into the barrel causes the actuator to move in a reversible manner, and moving the actuator in the reverse manner causes the plunger to pull outwards relative to its barrel. The invention also comprises various materials, methods of making, geometries and arrangements of parts, and accommodation of various specific existing syringe designs and applications.

26 Claims, 18 Drawing Sheets

U.S. PATENT DOCUMENTS

| | | | |
|---|---|---|---|
| 5,188,616 | A | 2/1993 | Nadal |
| D337,821 | S | 7/1993 | Tan |
| 5,469,860 | A | 11/1995 | De Santis |
| 5,492,535 | A * | 2/1996 | Reed et al. .............. 604/152 |
| 5,529,463 | A * | 6/1996 | Layer et al. .............. 417/403 |
| 5,582,595 | A | 12/1996 | Haber |
| 5,830,152 | A | 11/1998 | Tao |
| 5,891,052 | A | 4/1999 | Simmons |
| D411,882 | S | 7/1999 | Minasian |
| 6,231,550 | B1 | 5/2001 | Laughlin |
| 6,245,046 | B1 * | 6/2001 | Sibbitt ..................... 604/191 |
| 6,368,308 | B1 | 4/2002 | Nerney |

OTHER PUBLICATIONS

Shukla PK: A simple device for performing fine needle aspiration cytology. Indian J Pathol Microbiol 1993;36:433-435.

Vassilakos P, Schweblin JD, Albe X: A new syringe for fine needle aspiration biopsy. Acta Cytol 1993;37:29-33.

Sibbitt RR, Sibbitt WL Jr, Nunez SE, Kettwich LG, Kettwich SC, Bankhurst AD. Control and performance characteristics of eight different suction biopsy devices. J Vasc Intery Radiol. 2006;17:1657-69.

Nunez SE, Draeger HT, Rivero DP, Kettwich LG, Sibbitt WL, Jr, Bankhurst AD. Reduced pain of intraarticular hyaluronate injection with the reciprocating procedure device J Clin Rheumatol. 2007;13:16-9.

Bankhurst AD, Nunez SE, Draeger HT, Kettwich SC, Kettwich LG, Sibbitt, WL Jr. A randomized controlled trial of the reciprocating procedure device for intraarticular injection of corticosteroid. J Rheum 2007;34:187-92.

Sibbitt WL Jr, Sibbitt RR, Michael AA, Fu Di, Draeger HT, Twining JM, Bankhurst AD: Physician control of needle and syringe during traditional aspiration-injection procedures with the new reciprocating syringe. J Rheumatol. 2006;33:771-8.

Draeger HT, Twining JM, Johnson CR, Kettwich SC, Kettwich LG, Bankhurst AD. A randomized, controlled trial of the reciprocating syringe in arthrocentesis. Ann Rheum Dis. 2006;65:1084-7.

Nunez SE, Draeger HT, Kettwich SC, Kettwich LG, Bankhurst AD, Sibbitt WL: A randomized, controlled trial of the reciprocating syringe in local anesthesia. Journal of Emergency Medicine 2008 Available online Feb. 20, 2008.

Moorjani GR, Michael, AA, Peisjovich A, Park KS, Sibbitt WL Jr, Bankhurst AD: Patient pain and tissue trauma during syringe procedures: A randomized controlled trial. J Rheumatology 2008;35:1124-9.

Moorjani GR, Bedrick EJ, Michael, AA, Peisjovich A, Sibbitt WL Jr, Bankhurst AD: Integration of safety technologies into rheumatology and orthopedic practice: A randomized controlled trial. Arthritis Rheum 2008 (in Press).

Sander O. Intra-articular corticosteroid injections with the reciprocating procedure device reduced procedural pain and duration more than the conventional syringe. Evid Based Med. 2007;12:106.

Sibbitt RR, Palmer DJ, Sibbitt WL Jr. Introduction of Safety Technologies into Sclerotherapy of Varicose Veins. Vascular Endovascular Surgery (in Press 2008).

Michael AA et al. Syringe size: Does it matter in physician performed procedures?. Journal of Clinical Rheumatology 2008 (in Press).

Sibbitt RR, Palmer DJ, Sibbitt WL Jr., Bankhurst AD: Integration of new safety technologies into needle aspiration of breast cysts. Archives of Obstetics Gyn 2008 (in Press).

* cited by examiner

609

610

612

611

RECIPROCATING PROCEDURE SYRINGES

CROSS-REFERENCE TO RELATED APPLICATIONS

This application claims the benefit of U.S. provisional application 60/646,190, "Reciprocating Procedure Syringes," filed Jan. 21, 2005, incorporated herein by reference.

BACKGROUND OF THE INVENTION

Syringes are used to inject medications, to aspirate body fluids, to provide vacuum, and to transfer fluids. Many complicated medical procedures can benefit from the ability to use a syringe with one hand so that the other hand can be used for other tasks. However, aspiration with a standard syringe is difficult and awkward using one hand, resulting in loss of fine control and power during aspiration. A new design of syringe that permits both injection and aspiration with one hand, yet maintains fine motor control and the strength necessary to generate high pressures and vacuums would be a major advance in syringe technology.

Syringes can both inject or aspirate, but occasionally it can be important to fix or lock the plunger relative to the barrel in order to prevent the plunger from either going into the barrel (inadvertent injection) or out (inadvertent aspiration). To prevent this, various locking plunger designs have been proposed. See, e.g., U.S. Pat. No. 4,386,606 Tretinyak; U.S. Pat. No. 4,890,626 Wang. These plunger locks are particularly valuable for providing aspiration and holding a vacuum during needle biopsy procedures. See, e.g., U.S. Pat. No. 5,830,152 Liang-Che Tan; U.S. Patent D411,882 Minasian; U.S. Pat. No. 5,891,052 Simmons; U.S. Pat. No. 4,791,937 Wang; U.S. Pat. No. 4,874,385 Moran; U.S. Pat. No. 5,957,864 Oosterhof Most of these provide constant vacuum and suction, rather than variable vacuum.

First attempts at one-handed aspiration to provide variable vacuum involved the use of an external apparatus which is integral with the syringe and allows the plunger to be advanced or retracted using squeezing motions of the digits using one hand rather than pulling motion using two hands (U.S. Pat. No. 3,990,446. Taylor; Jewel Dean Randolph. 1976. Hypodermic syringe for stabilized aspiration by one hand.). Other patents create essentially the same device (U.S. Pat. No. 5,582,595. 1996. Haber; Terry M., Smedley; William H. Aspirating syringe having a plunger guide for a reciprocating plunger assembly.), and some use an adapter which can be fitted on a conventional syringe (U.S. Pat. No. 5,135,511. Houghton; Frederick C. 1992 Assembly for aspirating tissue, including adapter for syringe.) Several US patents (U.S. Pat. No. 4,484,915. 1984. Tartaglia; John A. Medical syringe; U.S. Pat. No. 4,639,248. Schweblin; Jean-Denis. 1987. Syringe, U.S. Pat. No. 6,368,308 Nerney Apr. 9, 2002 Syringe having forward-mounted plunger control; U.S. Pat. No. 4,594,073 Stine, Charles R. Jun. 10, 1986. Aspiration Syringe holder; U.S. Pat. No. 4,967,762 DeVeris, James H. Nov. 6, 1990. Biopsy syringe with suction vent; U.S. Pat. No. 5,115,816. Lee, Peter F. May 26, 1992. Single-hand controlled fine needle aspiration device; U.S. Pat. No. 5,469,860 De Santis, Stephen A. Nov. 28, 1995. Fine needle aspiration cytology device syringe holder; U.S. Pat. No. 5,498,246 Deutchman, Mark E., Deutchman Arnold H. Mar. 12, 1996. Aspirator/injector device with palm engaging handle; U.S. Pat. Des. No. 337,821, Jul. 27, 1993. Tan, Henry K. Fine needle aspiration biopsy gun.) describe a syringe with an external slide which attaches to the plunger, permitting one-handed operation.

All of the above designs are completely different in that they utilize a single piston and a single plunger. In addition, the position of the index and middle fingers as well as the thumb, must be moved on these syringes when switching from the aspiration to injection mode, resulting in intraoperative instability. In addition, during the single handed aspiration using these devices, the barrel and needle advance beyond the index and ring finger (loss of a stable platform), creating major difficulties in control and localization of the needle and resulting in instability and unpredictability during procedures. The present invention (the reciprocating, thumb-operated, double-plunger syringe) completely obviates the above problems by providing a stable platform for both injection and aspiration with the index and middle fingers in a fixed position, with the only required movement being a lateral movement of the thumb to the reciprocating plunger.

Other patents describe more complicated two compartment syringes and double plunger syringes, but these are usually based on a single barrel and are intended to mix or administer two different substances (U.S. Pat. No. 3,685,514: Cheney; Paul E. 1972. Two Compartment Syringe; U.S. Pat. No. 5,188,616: Nadal; Guy. 1993. Syringe with double plunger.). Others describe double piston devices (U.S. Pat. No. 4,036,232: Genese Joseph Nicholas 1977. Aspiration device; U.S. Pat. No. 4,437,859: Whitehouse; Craig M., Cox; Nigel, Burt; Allan G., Snyder; Daniel R.: 1984. Hydraulic syringe drive.), either mechanically or hydraulically driven, for aspirating fluids or administering medications.

Only three previous patents describe the basic reciprocating syringe (U.S. Pat. No. 6,245,046 B1 Sibbitt, Wilmer L. Jr.: Reciprocating Syringes, Jun. 12, 2001, U.S. Pat. No. 6,962, 576 B1: Reciprocating syringes. Sibbitt, Wilmer L. Jr. Issued Nov. 8, 2005, and U.S. Pat. No. 6,231,550 Laughlin, Joshua May 15, 2001 One-handed single grip position aspiration and injection syringe) with the Sibbitt patents being dominant in terms of filing priority. The reciprocating syringe is characterized by two plungers, plunger equivalents, or parallel longitudinal members that are mechanically bound together so that they move in a reciprocating (alternating) fashion, so that when one plunger goes up the other goes down by the use of a pulley system, gears, hydraulics, or other mechanisms upon flexion of the thumb (U.S. Pat. No. 6,245,046 B1 Sibbitt, Wilmer L. Jr.: Reciprocating Syringes, Jun. 12, 2001, U.S. Pat. No. 6,962,5766 B1: Reciprocating syringes. Sibbitt, Wilmer L. Jr. Issued Nov. 8, 2005). This permits the syringe to be operated with one hand for both injection and aspiration. The present invention comprises refinements in reciprocating syringe design, the conversion of conventional syringes to reciprocating syringes, methods of production of reciprocating syringes, and the specific application of plunger locks to reciprocating syringes and other improvements all of which have special implications for syringe based procedures.

SUMMARY OF THE INVENTION

The present invention provides a reciprocating syringe that can be used in connection with existing syringe barrels and fittings. In some embodiments, the syringe can comprises a frame, adapted to retain two existing syringe barrels. The frame can accommodate fittings (e.g., needles) on one or both barrels, in various embodiments of the present invention. The invention also provides a plunger complex, comprising two plungers, each adapted for use with one of the syringe barrels. The two plungers are coupled such that pushing of each plunger into its barrel causes the other plunger to pull outwards relative to its barrel. The two plungers can be coupled by a flexible line attached to one plunger, routed from the plunger out of the corresponding barrel into the other barrel, and attached to the other plunger. The invention contemplates various configurations of the frame to accommodate desired line and pulley performance characteristics.

In other embodiments, the syringe comprises a frame adapted to retain an existing syringe barrel, and an auxiliary actuator mounted with the frame. Such an actuator can provide a syringe-like plunger operation, or can comprise other manipulable structures. The auxiliary actuator can be coupled to a plunger adapted for use with the syringe barrel, such that pushing the plunger into the barrel causes the actuator to move in a reversible manner, and moving the actuator in the reverse manner causes the plunger to pull outwards relative to its barrel.

Parallel actuation can lead to interference between plungers or actuators in operation, and can lead to inconvenient manual manipulation due to constrained space for the operator's fingers. The invention also contemplates arrangements of the two barrels, or the barrel and an auxiliary actuator, such that the axes of operation are nonparallel. In some embodiments, the two axes of operation diverge from each other, such that the operable ends of the plungers/actuator are separated by a more convenient distance.

Some conventional syringe barrels have markings, e.g., markings to indicate volume displaced. Some embodiments of the present invention comprise a frame having an optically transmissive portion that allows such markings to be seen even when the barrel is retained by the frame. Such optically transmissive portions can include cutout areas of the frame, and optically transparent areas (windows) in the frame. The invention also comprises various materials, methods of making, geometries, and accommodation of various specific existing syringe designs and applications, examples of which are described below.

Advantages and novel features will become apparent to those skilled in the art upon examination of the following description or may be learned by practice of the invention. The advantages of the invention may be realized and attained by means of the instrumentalities and combinations particularly pointed out in the appended claims.

DETAILED DESCRIPTION OF THE INVENTION

Figure 1:
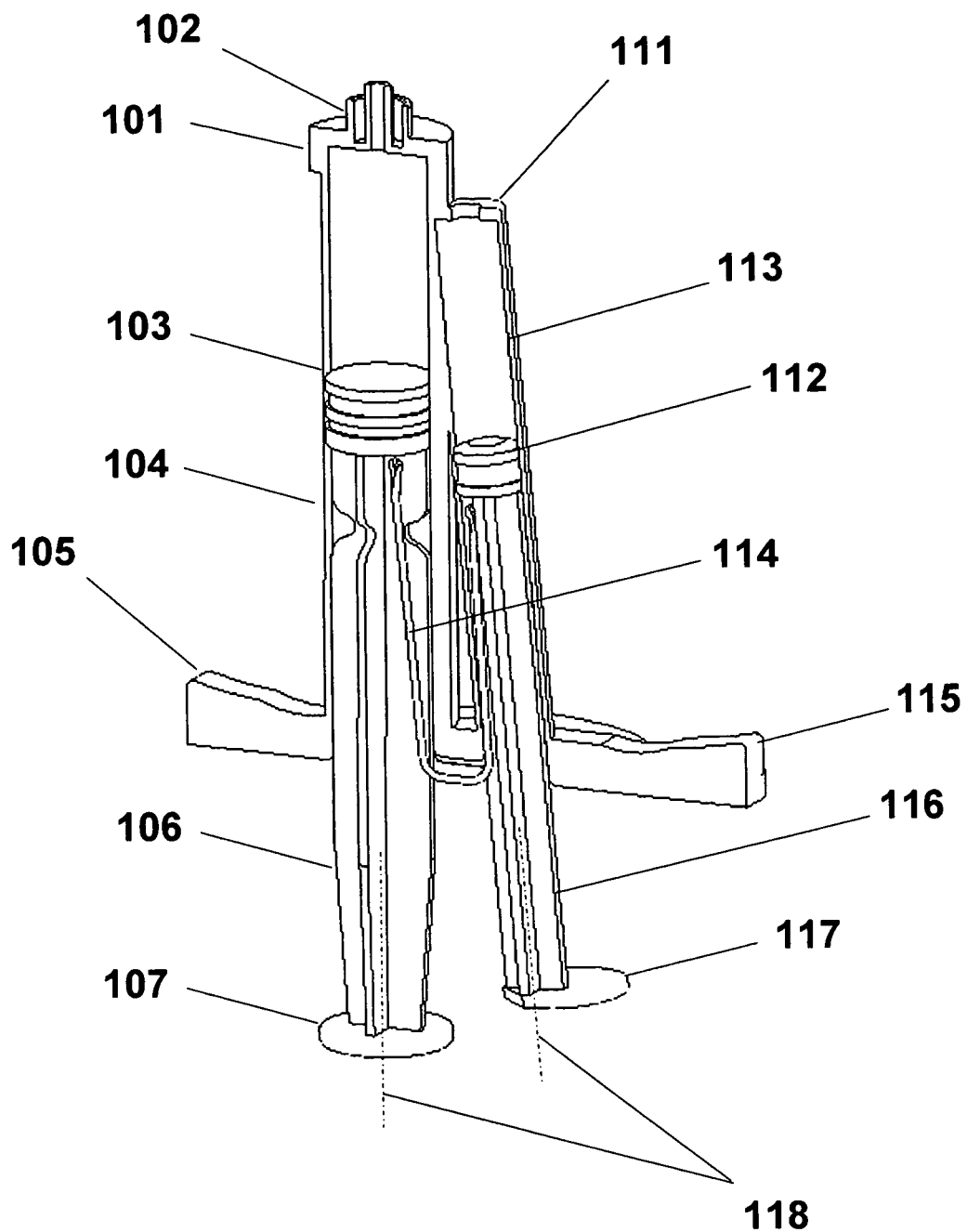
FIG. 1 is a schematic illustration of a reciprocating syringe according to the present invention with non-parallel, angled barrels or tracts, stopper/drag devices, and asymmetrical thumb rests.

Syringes are an essential element in the day to day practice of medicine and nursing, but are also essential in industry, laboratory science, research, and animal husbandry. Syringes are used to inject medications, to aspirate body fluids, to provide vacuum, and to transfer fluids. The syringe design most commonly used in medicine consists of a barrel made of plastic and an internal plunger which is moved into or out of the barrel, resulting in pressure or a vacuum, respectively. The difference in pressure between the volume in the syringe and the outside environment are produced by movement of the plunger, resulting in movement of fluid into or out of the syringe. These differences in pressure create the desired effect of a syringe, that is, aspiration or injection.

Injection with a standard syringe is simple, and uses the powerful flexor muscles of the hand and forearm. Injection with a standard syringe can usually be accomplished with one hand, freeing up the other hand for other necessary tasks or procedures. In this technique the 2nd (index) and 3rd fingers (middle finger) are placed on the finger flange of the syringe and the thumb is placed on the thumb rest of the plunger. The digits are brought together resulting in a powerful injection due to contraction of the powerful flexor muscles of the hand and forearm. The ability to use a syringe with one hand in this way and use the other hand for other tasks is important in many complicated procedures.

Aspiration with a standard syringe usually requires the use of two hands in order to generate the necessary power and maintain fine control. Generally, this is done by using one hand to control the barrel and the other hand to pull on the thumb rest of the plunger. The two handed technique uses the muscular strength of both the hands and the arms, thus, very powerful vacuums with rapid movement of fluid into the syringe can be obtained. This technique is often used when either fine control of the syringe is required or considerable power is necessary.

One-handed aspiration with a standard syringe is possible, but can be difficult and awkward. One of two different techniques is generally used. In a first method the thumb rest of the plunger is grasped by the 2nd and 3rd digits (index finger and middle finger) and the thumb is placed on the finger flange of the syringe. The fingers are forcefully flexed, while the thumb remains extended. This results in the plunger be pulled out, resulting in an effective aspiration. There are several problems with this method including 1) fine control of the syringe is effectively lost (which can be important when there is a sharp needle in delicate living tissues), 2) the entire syringe tends to rotate, further degrading control, 3) due to the size of the syringe components relative to the dimensions and strength of the human hand this method can be extremely difficult with syringes larger than 10 cc (i.e., 20 cc or 60 cc), and 4) the force of aspiration is generated by the weak intrinsic flexors of the hand (without using the powerful flexors of the thumb and forearm), resulting in a weaker aspiration. Thus, this one-handed method is unsatisfactory for many applications.

One-handed aspiration can also be accomplished by the alternative thumb method. In this method, the syringe barrel is grasped by the four fingers, and the thumb is placed under the thumb rest of the plunger. With the syringe firmly grasped by the digits the thumb is extended, resulting in aspiration. The alternative thumb method has several disadvantages: 1) although a degree of control is maintained, it is not the fine control of the fingers, but the more coarse control of the forearm musculature, 2) the power of the aspiration is weak, because it is accomplished by the weak extensors of the thumb, 3) full aspiration is difficult to achieve without changing the handgrip, 4) the syringe is generally pointing toward the operator which is the opposite from direction required in a medical procedure (except for a person injecting themselves with drugs), and 5) when the thumb is extended the hypothenar tissues are compressed under the syringe, resulting unpredictable deviation of the needle side of the syringe with some loss of control.

With either technique, one-handed aspiration with a standard syringe is difficult and awkward, resulting in loss of fine control and power during aspiration. With loss of control, there is a higher rate of procedure failure and contamination. With loss of power, speed of aspiration is impaired, especially for viscous fluids. Because of the loss of strength and control with one-handed aspiration, procedures that demand either fine control of the syringe during aspiration or the generation of a powerful vacuum require the use of both hands during aspiration to maintain both strength and control. A syringe that permits both injection and aspiration with one hand, yet maintains fine motor control and the strength necessary to generate high pressures and vacuums would be a major advance in syringe technology.

Although three previous patents describe a basic reciprocating syringe (U.S. Pat. No. 6,245,046 B1, Sibbitt "Reciprocating Syringes," issued Jun. 12, 2001; U.S. Pat. No. 6,962, 5766 B1: Reciprocating syringes. Sibbitt, Wilmer L. Jr. Issued Nov. 8, 2005; and U.S. Pat. No. 6,231,550, Laughlin, issued May 15, 2001 "One-handed single grip position aspiration and injection syringe"), refinements, conversions, methods of production, and plunger locks with reciprocating syringes have not been described previously. The present patent describes refinements in reciprocating syringe design, the conversion of conventional and specialty syringes to reciprocating syringes, methods of production of reciprocating syringes, and the specific application of plunger locks to reciprocating syringes, all of which have special implications for syringe based procedures.

A reciprocating syringe can be characterized by two plungers, plunger equivalents, or parallel longitudinal members that are mechanically bound together so that they move in a reciprocating (alternating) fashion: when one plunger goes up the other goes down, coupled by mechanisms such as a pulley system, gears, or hydraulics. The present invention concerns methods of production, improvements, and special embodiments of reciprocating syringes. The present invention includes reciprocating syringes with non-parallel barrel or tracks, stopper/drag devices, asymmetrical thumbrests, design and construction of a pulley-driveline plunger complex, self-threading and enclosed pulleys, methods to construct of a barrel complex, an external frame or housing to create the barrel complex, locking plungers, introducer fittings, and methods to construct reciprocating safety syringes, Menghini needle syringe, and methods of production and embodiments of reciprocating versions of conventional and specialty syringes.

The present invention can provide a syringe that permits injection and aspiration of fluids or gas using one hand, and has applications to health care, research, and industry. The present invention utilizes an internal or external accessory plunger or plunger equivalent (member) with or without an accessory barrel (or track), which is mechanically associated with the plunger of a functional syringe, resulting in a set of reciprocating plungers. When the functional plunger is depressed with the thumb, the functional syringe injects; when the accessory plunger is depressed with the same thumb, the functional syringe aspirates. This permits the index and middle fingers to stay in one position during aspiration and injection, while the thumb only need move laterally to between the functional and accessory plungers to change the direction of aspiration or injection. The resulting syringe is highly stable since only the thumb position changes, and very powerful vacuums or pressures can be developed since the powerful flexors of the fingers, thumb, and forearm are used for both aspiration and injection. The syringe can be used with one hand, and can be used in all cases where standard syringes are used. The syringe offers particular advantages in medical procedures when one-handed injection/aspiration is required (such as cardiac catheterization, emergency procedures, certain types of surgery, pediatric and veterinary procedures and in those handicapped individuals who can only use one hand). The invention includes reciprocating syringes with non-parallel barrel or tracks, stopper/drag devices, asymmetrical thumbrests, design and construction of the pulley-driveline plunger complex, self-threading and enclosed pulleys, methods to construct of the barrel complex, external frame or housing to create the barrel complex, locking plungers, introducer fittings, and methods to construct reciprocating safety syringes.

Example Embodiment

Nonparallel Plungers, Asymmetrical Thumb Rests, Added Drag

U.S. Pat. Nos. 6,245,046 B1, 6,962,576 B1, and 6,231,550 describe reciprocating syringes with parallel barrels or tracts for the movement of the reciprocating plungers, plunger equivalents, or reciprocating members. The reciprocation can be effected by multiple mechanical means including static and non-static pulley systems, gear systems, pneumatics, and other mechanical means, powered by motion of the human thumb. However, it is not necessary for the barrels or tracts to be strictly parallel to permit this reciprocating motion, rather, reciprocation can be effected by the orientation in non-parallel tracks completely analogously to the parallel barrel/tract previously described. An example embodiment with non-parallel plungers is depicted schematically in FIG. 1. A dominant syringe 101 comprises a needle fitting 102; a stopper/drag device 103 on the plunger; a functional barrel 104; a finger flange 105; a functional plunger 106; and a symmetrical or asymmetric thumb rest 107. An accessory syringe comprises an accessory barrel or track 111, with or without needle fitting; a stopper/drag device 112 on an accessory plunger; a non-parallel barrel or track 113 for accessory plunger, plunger-equivalent, or reciprocating member; a reciprocating mechanical link between plungers (pulley, gear, hydraulics, or mechanism) in this case monofilament pulley mechanism 114 attached to both plungers; a finger flange 115; an accessory plunger 116, plunger equivalent, or reciprocating member, a symmetrical or asymmetric thumb rest on accessory plunger 117; with the barrels, tracks, plungers, plunger-equivalents, or reciprocating members mounted at an angle 118 to each other.

Non-parallel reciprocating syringes such as that in FIG. 1 are roughly similar to the parallel reciprocating syringes previously disclosed, but non-parallel syringes permit the plungers, plunger equivalents, or reciprocating members to move either towards each other or away from each other, depending on the angle between the two barrels or tracks and the cycle of reciprocation. With parallel reciprocating syringes, the plungers, thumb rests, and thumbs can interact deleteriously (e.g., interfere with each other) during a reciprocating cycle. This can cause device instability and loss of control of the syringe. With non-parallel barrels or tracts, the interference between the plungers, thumb rests, and thumbs can be reduced by the angle between the two barrels or tracts. Angling the barrels away from each other can result in an increased distance between the plungers, thus reducing deleterious interaction between the plungers, thumb rests, and thumbs.

FIG. 1 demonstrates this beneficial effect. A dominant, or functional, syringe 101 has a conventional relationship with a needle fitting 102. An accessory barrel or track 111 mounts with the dominant syringe 101 at an angle 118 thereto. The angled mounting relationship causes the two plungers 106, 116, and consequently the corresponding thumb rests 107, 117 to be non-parallel, and thus separated at the distal ends by a distance d. Unlike previously described parallel barrel or track reciprocating syringes, this distance d is greater than the sum of ½ the diameter of the functional barrel and ½ the diameter of the accessory barrel or tract, effectively increasing this distance between the two plungers and respective thumb rests. The increased distance reduces interference between the two plungers, thumb rests, and the thumb, and, thus, facilitates smooth syringe motion and functioning. An angled relative mounting like that described in this example can be used to generate a reduced interference variant of parallel reciprocating syringes, and to generate a reduced interference variant of any double plunger syringe (including non-reciprocating syringes).

Asymmetrical thumb rests 107, 117, as shown FIG. 1, can also help to decrease interference. The thumb rests 107, 117 can be asymmetrical in terms of the relationship of their midpoint to the underlying midline of the corresponding plunger device 106, 116. Suitable thumb rests can be shaped in various ways, including circular, oval, rectangular, elliptical, off-set from center or not, as well as many other geometrical shapes. One or both thumb rests can be asymmetrical. Asymmetrical thumb rests can also have other functions, including being a component of a plunger lock, as described elsewhere herein.

Some previous reciprocating syringes have performance limitations due to low drag in operation, allowing the plungers to move spontaneously or with little force, causing dysfunction of the device. Unintended movement with minor forces is usually not a problem with the functional plunger 106 because the stopper 103 typically provides considerable drag or static friction which tends to discourage movement of the plunger. However, the accessory plunger 117 in previous reciprocating syringes typically did not provide adequate drag to resist movement spontaneously or with only minor forces. This can cause instability or dysfunction of the device, and in the case of a pulley mechanism, redundancy in the drive line. Some embodiments of the present invention can prevented by placing a drag mechanism 112 on the accessory plunger 116. In the example shown in the figure, a conventional syringe stopper provides the desired drag. In other examples, the drag mechanism can be an incomplete stopper (if a pneumatic seal is not necessary), or a ring, band, protuberance, or other shape attached to either the plunger or lining the accessory barrel or track. The drag mechanism can comprise a resilient or compressive-expansive material such as rubber, synthetic plastics with rubber-like properties, foam, or even mechanical devices that provide the desired drag. In the case of accessory plunger or plunger equivalent anchored on the outside of a functional syringe barrel by a complete or incomplete band attached to the accessory plunger (as described in U.S. Pat. No. 6,231,550) a drag mechanism can be on the external surface of the functional syringe, the retaining band of the accessory plunger or driver, on the internal surface of the accessory plunger, or in the track for the accessory plunger in the finger flange of the syringe. Drag devices according to the present invention can markedly improve the function of reciprocating syringes and related devices by reducing unintended motion, preventing redundancy in the drive line, and optimizing smooth, controlled motion, and are generally applicable to two plunger, two plunger equivalent, and two driver reciprocating devices.

Example Embodiment

Pulley/Drive Line/Plunger Complex

Figure 2:
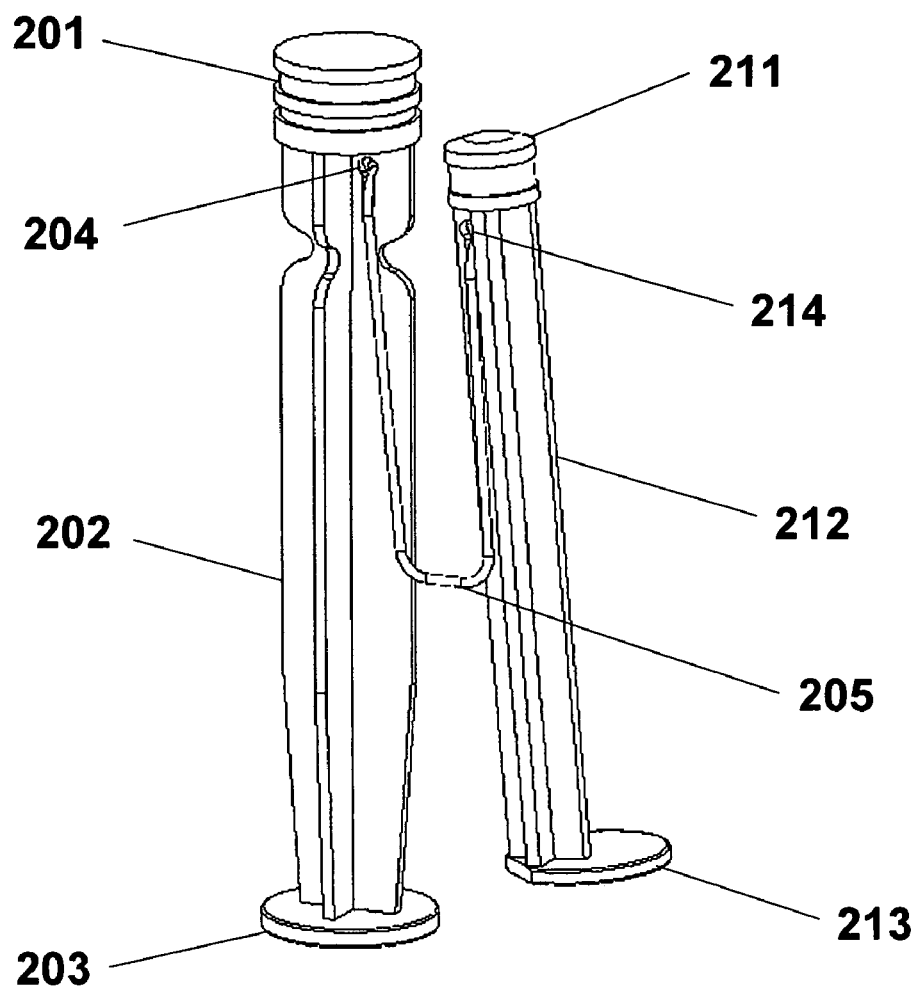
FIG. 2 is a schematic illustration of a pulley drive line and plunger complex according to the present invention.

Some reciprocating syringe designs employ a pulley mechanism that mechanically binds the two plungers or plunger equivalents so that these two members move in a reciprocating fashion. FIG. 2 is a schematic illustration of a typical pulley driveline-plunger complex, referred to herein as a plunger complex. The plunger complex comprises a dominant plunger 202, an accessory plunger or plunger equivalent 212, a drive line 205, and attachments for the drive line into the plungers 204, 214. The attachment areas are illustrated towards the stopper ends of the plungers 201, 211, but can be anywhere on the plungers depending on the particular construction and dimension of the pulley device between the two barrels or tracts. The plungers 202, 212 further comprise thumb rests 203, 213.

In some embodiments, the plungers can comprise separate parts, e.g., conventional syringe parts or specially molded parts. The drive line in some embodiments comprises a continuous columnar filament or other continuous material, attached to the plungers in any of various ways. The drive line can be welded or cemented to a plunger. The drive line can be placed through a hole or notch in the plunger and then the drive line fixed so that it does not pull through the hole or notch, for example by tying, welding, cementing, or distorting the drive line with heat or mechanical means. The drive line can be clamped with mechanical clamps to the plunger. The plunger can comprise hooks, rings, grommets, slots, keyhole structures (joined slot and hole), male or female fittings, compressive mechanisms or other similar devices to which the drive line is attached by tying, welding, crimping, friction, maneuvering, or mating of the male and female connectors. The drive line and plunger can have complementary (male-female for example, key and keyhole) fittings which attach when the fitting are brought together, e.g., by pushing the connectors together or pushing and then pulling to the slot. Such connectors can be attached to and made in the plunger and/or line after each piece is produced, or can be molded as an integrated part of a component when the component is produced (e.g., molded or extruded).

The plunger complex can also be molded as one integrated part. With the choice of an appropriate plastic, the entire plunger complex including drive line, dominant plunger, and accessory plunger can be injection molded as one integrated part. Alternatively, an appropriate temperature resistant drive line can be placed into the mould, and then the two plungers molded around it, resulting in a high temperature bond between the plungers and drive line and an integrated device. The plungers themselves can be solid, strutted (as in most conventional syringes), columnar, hollow, or take a number of other geometrical shapes as long as they accommodate and are complementary to the design of the barrel and/or tracks.

Example Embodiment

Self-Threading and Line-Retaining Pulleys

The pulley mechanism of a reciprocating syringe generally rests between the two barrels or tracks and permits low friction movement of the drive line over its surface as the plungers move. Such a pulley can take a number of forms, but a static version as described in U.S. Pat. No. 6,245,046 B1 is considered economical and practical. Whatever pulley mechanism is used, however, it is important that the drive line stay in the track even when there is drive line redundancy. Drive line redundancy can occur when assembling the syringe or when a plunger is pulled. The drive line in a redundancy condition can slip out of the pulley mechanism. When tension is placed on the drive line again by depressing one of the plungers, if the drive line does not properly align itself in relation to the pulley, the device can become misaligned, exhibit increased drag or resistance to desired motion, and can fail to function properly.

Figure 3A:
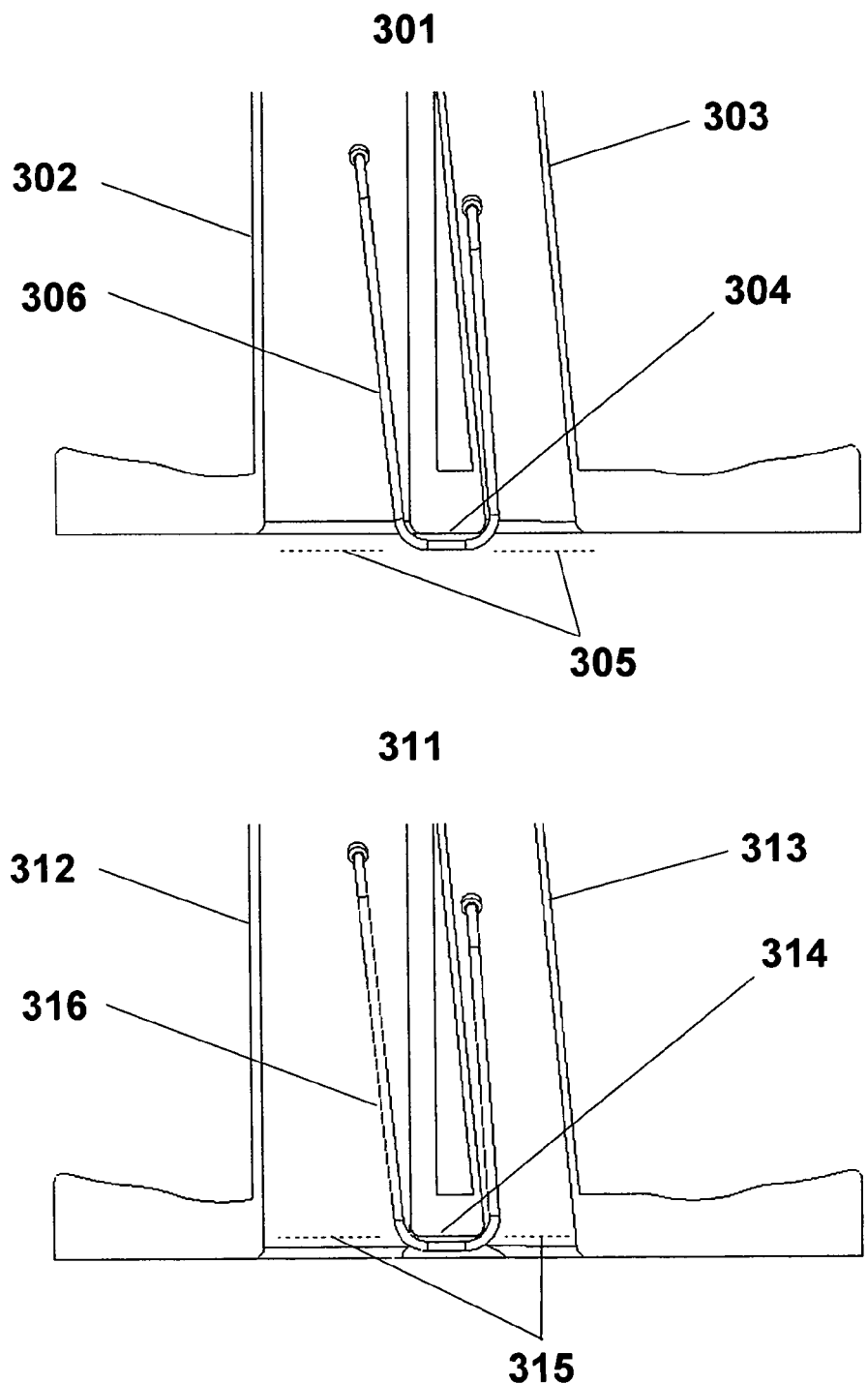
FIG. 3(a,b) is a schematic illustration of self-threading pulleys according to the present invention.
Figure 3B:
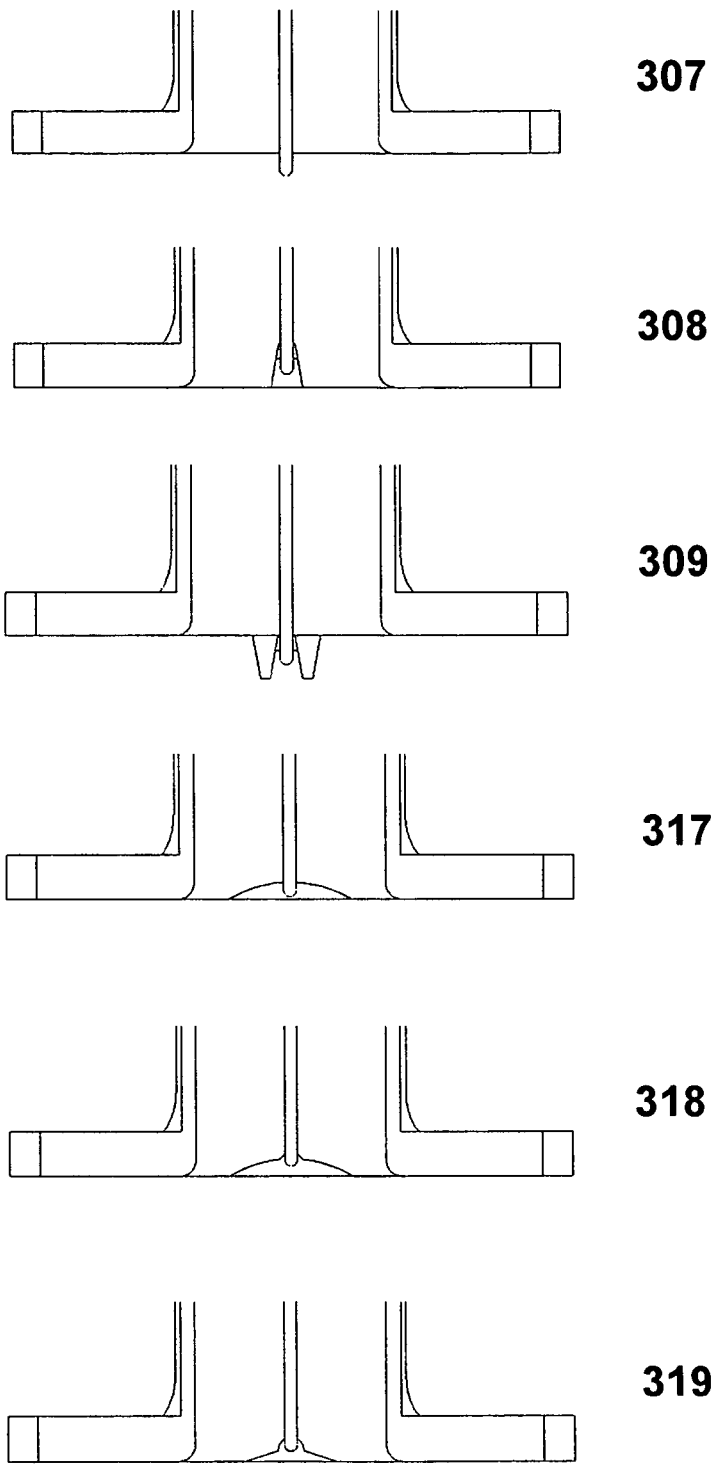

The potential for problem is illustrated schematically in FIG. 3. A cross-sectional view through the finger flanges of a reciprocating syringe 301 depicts a dominant barrel 302, an accessory barrel 303, a pulley 304, and a drive line 306. The static or dynamic pulley 304 is created by the junction of the dominant barrel 302 and accessory barrel 303. The pulley can have a conventional barrel surface, a smooth contiguous surface 307 created by molding of the barrels or by a frame that encloses the barrels, by a groove 308 to control the drive line position, or by a protuberance with a groove 309 for the same purpose. In prior configurations the pulley is at the level of or above 305 the native barrel wall. In a condition of drive line redundancy, the drive line can be displaced from the pulley, and fail to properly realign when tension is subsequently placed on the drive line.

Some embodiments of the present invention can preclude such problems by providing a self-threading pulley. A self-threading pulley can be provided by making the surface of the junction of the two barrels lower than the native or surrounding surface, creating a funnel effect in which tension on the drive line will urge the drive line into the appropriate pulley position. Example embodiments of simple self-threading pulleys are shown schematically in FIG. 3(a,b). A cross sectional view through the finger flanges of a reciprocating syringe 311 with a self-threading pulley device depicts a dominant barrel 312, an accessory barrel or track 313, a static or dynamic pulley 314 below level of native barrel walls 315, and a drive line 316. The static or dynamic self-threading pulley can be provided below the level of the native barrel walls or frame 315 (or simply lower than adjacent areas on the syringe surface), creating a funnel effect, which mechanically urges the drive line into the correct position. Additional cross sectional views through the midline of the syringe in the plane of the self-threading pulley device showing drive line over the surface of a self-threading pulley created by (1) curved or slanted barrel junction walls 317, (2) a recessed groove in curved barrel junction walls 318, and (3) a recessed groove in slanted barrel junction walls 319. Other configurations are also possible, that have laterally higher surfaces and lower midline surfaces, all of which can urge the drive line into the intended pulley surface or track when tension is placed on the drive line. These self-threading pulleys can be static or dynamic. Alternatively the pulley surface can be made substantially flat or semi-columnar so no groove is necessary.

The drive line can also be surrounded or enclosed by a complete or partial retaining band, guide, or enclosed track at the pulley point, any of which can prevent unwanted migration of the drive line. Such line-retaining pulleys, however, can be more difficult to assemble than self-threading pulleys. Self-threading and line-retaining pulleys can decrease assembly time of the devices and can reduce the chance of device failure or malfunction. Similar self-threading and retaining pulleys can have mechanical applications beyond reciprocating syringes.

Example Embodiment

Frame-Based Reciprocating Syringes

The barrel complex of a reciprocating syringe can be produced similarly to the production of a conventional syringe barrel. Injection molding can be an efficient manner of production with plastics and other injectable, form-fitting materials. The entire barrel complex, including the dominant barrel, finger flanges, and accessory barrel or track, can be injection molded in one piece. A dedicated mould for the entire barrel complex can obviate barrel complex assembly, thus reducing production costs. Dimensional tolerances in such a mold must be very fine because the syringe parts must fit exactly to maintain pressure/vacuum integrity. Also, generally a specialized mold is necessary for each different size or type of reciprocating syringe.

A frame-based reciprocating syringe can be an alternative to previous methods of production (including assembly of intermeshing, complementary parts, by cementing, by welding; and by injection molding in one or several pieces). A frame can be produced, optionally with an integrated accessory barrel or track, that fits wholly or partially around or binds with an essentially conventional syringe barrel. The frame can rigidly anchor the syringe barrel in relation to the accessory barrel or track, creating the barrel complex. Such a frame or housing can comprise permanently fixed or temporary, releasable clamps, rigid passive fittings, a hinged enclosure device, and flexible, plastic, rigid, rubber, or resilient fittings that can accommodate a conventional barrel or barrels and restrain it within or on a rigid framework (which can be the accessory barrel or track), or locking mechanisms such as dentates and other mechanical mechanisms so that a conventional syringe can be bonded to a frame and the resulting dominant barrel can be fixed in relation to the accessory barrel or track. A frame-based structure can provide a reciprocating syringe device in which conventional syringes can be replaced as necessary (a reusable reciprocating frame), or alternatively, can be permanently fixed to the syringe, creating a disposable reciprocating syringe.

In the case of a reciprocating syringe with a pulley, the pulley device can be on the frame, and in alternative versions with gears, pneumatics, and rack-and-pinion devices, these devices can also be part of the frame. A particular advantage to the approach of an external frame that seats a substantially conventional syringe into a disposable or reusable reciprocating syringe, is that reciprocating versions of many existing syringes can be made easily and cheaply using molds for the frames which are much less expensive than creating an expensive precision mold that includes the syringe barrel itself. This also permits disparate materials to be assembled into a reciprocating syringe, including glass, plastic, and other specialty materials.

Figure 4:
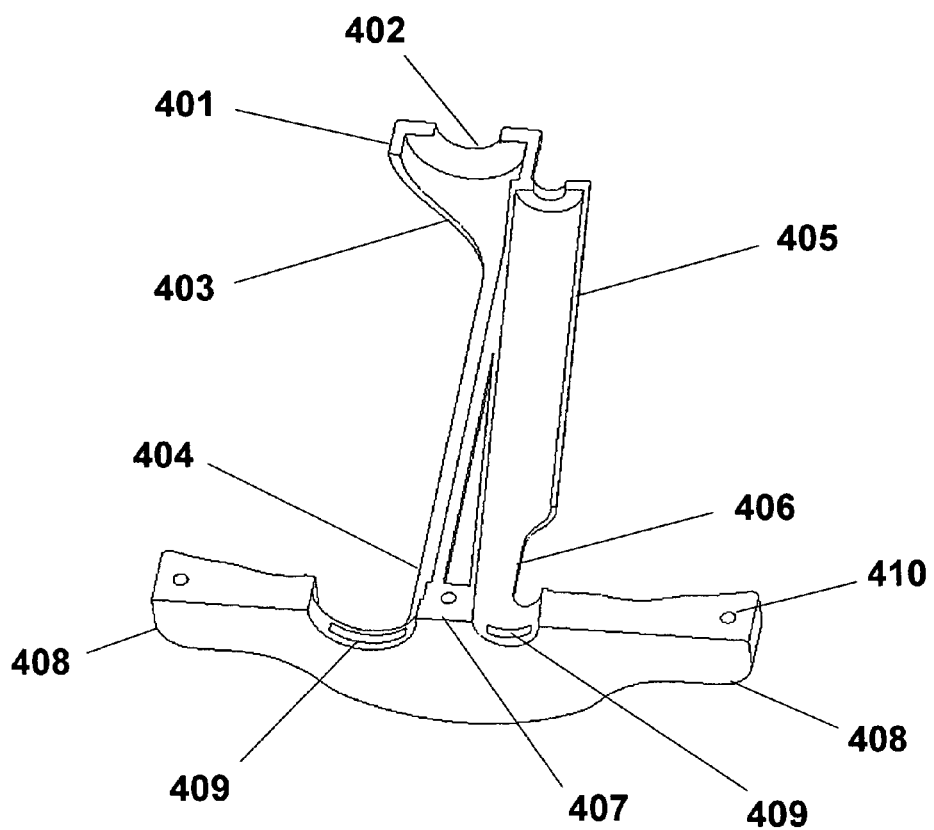
FIG. 4 is a schematic illustration of a syringe apparatus according to the present invention having an external frame or housing as a basis of the barrel complex.

FIG. 4 is a schematic illustration of an example of such a frame. The example frame comprises two essentially mirror-image halves that can be cemented or welded together. They can also be held together by clips, restraining bands, locking devices, interdigitating members, or even molded around existing syringes. The parts of the frame or housing can enclose the syringes as shown in the example. The frame can also just hold the syringes without fully enclosing them, and in that case can more easily be formed as a single piece. In the example of FIG. 4, the accessory barrel or track consists of another syringe barrel or a part of a barrel that can be inserted into the frame or housing. The accessory barrel can also be an actual part of the housing, rather than an exogenous barrel that is inserted. There are matching portions of the frame or housing to accommodate the needle fitting and the finger flanges of the conventional syringe, but other rigid designs are possible and anticipated.

FIG. 4 presents superior and oblique views of one half of a frame or housing to create a reciprocating syringe from a conventional syringe. The two parts not need be identical or mirror image, as in the example shown, as long as they hold the syringe barrel and accessory barrel or track firmly in relationship to each other. The frame or housing can consist of just one part, as in a syringe holder, but instead of accommodating one barrel can accommodate the dominant barrel and the accessory barrel or tract, or can have the accessory barrel or track integrated into the frame or housing. FIG. 4 shows one example of a specific housing for dominant syringe barrel 401, an appropriate opening for syringe needle fitting 402. The material can be clear transparent/translucent, or can be tinted or opaque with an optional cut-away to expose volume markings on the seated syringe 403. The frame can be formed such that it permits the fingers to be closer together, thus creating a digit grip 404. A housing 405 is also present for an accessory barrel or track (although the housing can contain a barrel or track integrated with the housing) in which the accessory plunger or plunger equivalent can move; optionally formed to provide a digit grip 406. The frame provides a static or dynamic pulley (or in the case of other embodiments, a gear or pneumatic track) 407, finger flanges 408, anchor slits 409 to accommodate and fix the finger flanges of syringe barrels placed into the frame or housing, and bonding points 410 where the frame parts can be bonded, cemented, clipped, interdigitated, or otherwise bound together. This frame or housing can be skeletonized by providing only such material as is required for strength, and can be made of various materials including plastic, metal, glass, and/or composites.

Figure 5:
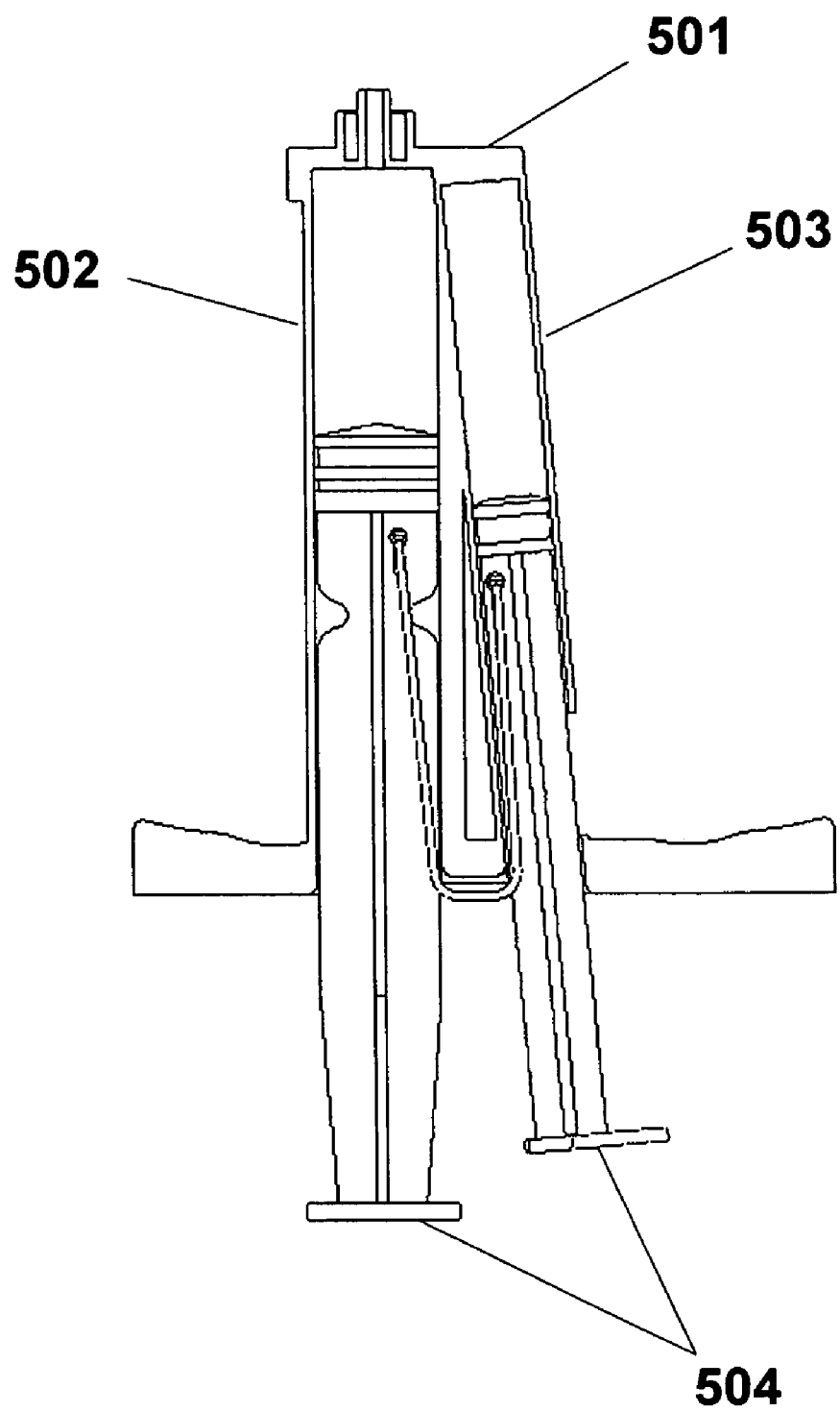
FIG. 5 is a schematic illustration of an assembled syringe apparatus as in FIG. 4.

Frames or housings of other designs are anticipated, all providing for fixed relative positioning of the dominant barrel and the accessory barrel or track. Other design changes, including parallel or non-parallel relationships of the dominant and accessory barrels or tracks can be also be accommodated in such a frame or housing. FIG. 5 is a schematic illustration of a frame or housing 501 accommodating a conventional syringe as the dominant syringe 502, and the accessory barrel or tract being a smaller conventional syringe with the needle fitting removed 503, and the two plungers mechanically linked with a drive line and pulley mechanism 504.

Figure 13A:
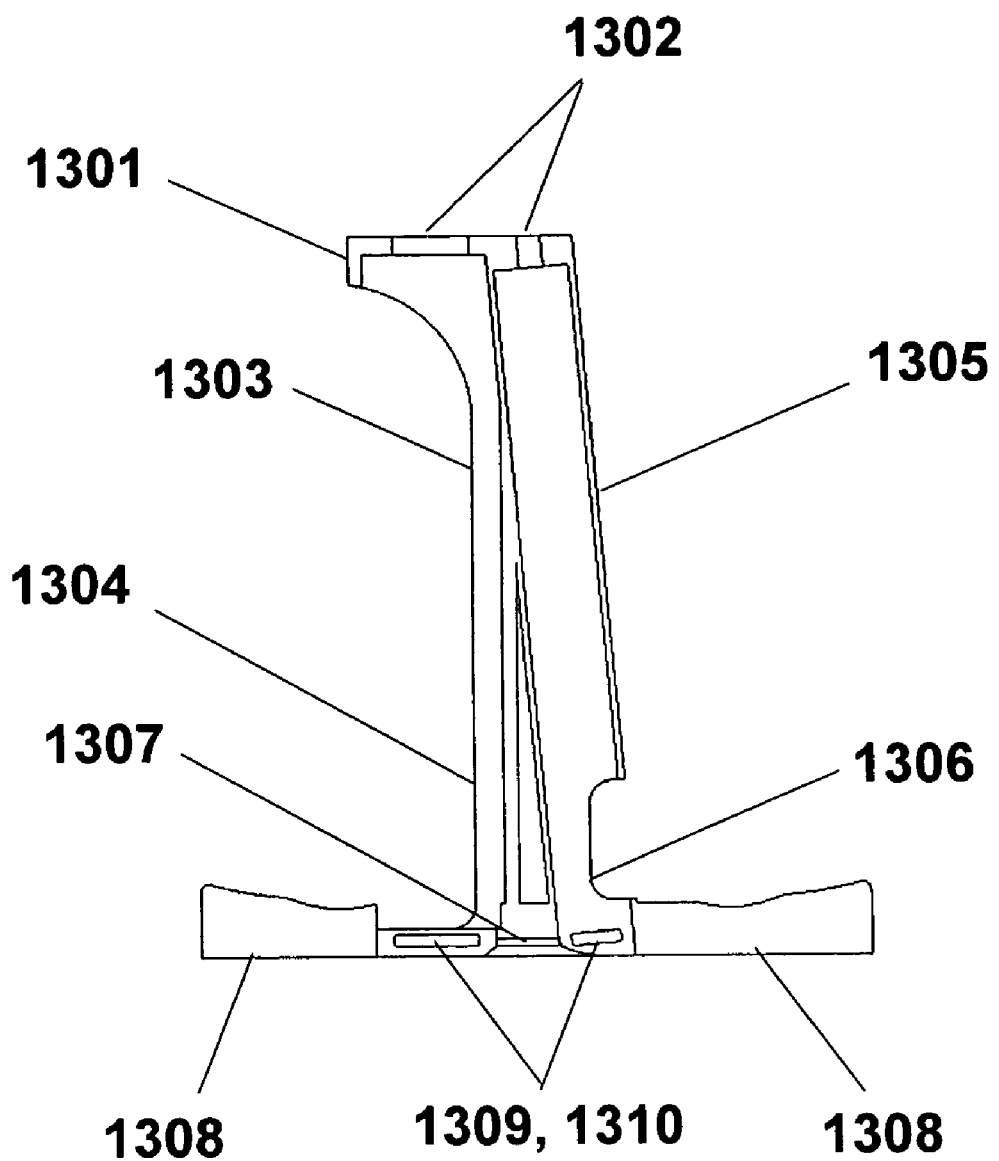
FIG. 13(a,b,c) comprise schematic illustrations of barrel complex variations according to the present invention.

FIG. 13(a,b,c) comprises schematic illustrations of variations in construction of the barrel complex. FIG. 13a illustrates a one-piece frame in which conventional or non-conventional syringes can be inserted and bonded with retaining devices as discussed above. The frame includes a housing for a dominant syringe barrel 1301, an opening for a syringe needle fitting 1302, a cut-away region to expose syringe volume markings 1303, a cut-away region for a digit grip 1304, a housing for a functional or non-functional accessory driver syringe barrel 1305, a cut-away for a digit grip 1306, a static or dynamic pulley 1307, finger flanges 1308, anchor slits for finger flanges of syringe barrels 1309, and locking mechanisms to hold dominant and accessory syringe barrels in the holder 1310.

Figure 13B:
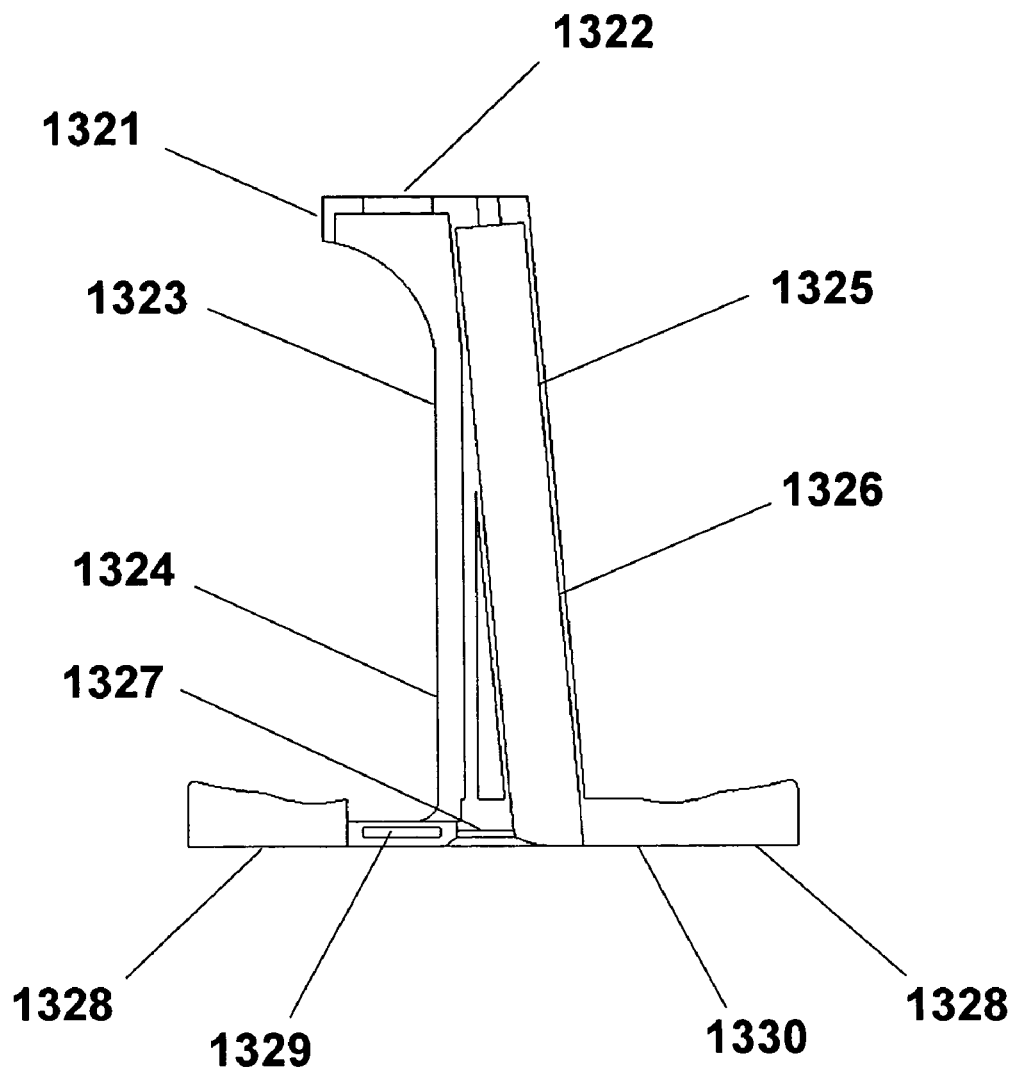

FIG. 13b illustrates a one piece frame in which only the dominant syringe is inserted and the accessory barrel is integrated with the frame. The frame has an integrated accessory barrel and a housing for a dominant syringe barrel 1321, an opening for a syringe needle fitting 1322, a cut-away region to expose syringe volume markings 1323, a cut-away region for a digit grip 1324, an internal barrel of a non-functional accessory driver syringe 1325, an outer surface of the accessory barrel 1326, a static or dynamic pulley 1327, finger flanges 1328, anchor slits for finger flanges of the dominant syringe barrel 1329, and locking mechanisms to hold dominant syringe barrels in the holder 1330.

Figure 13C:
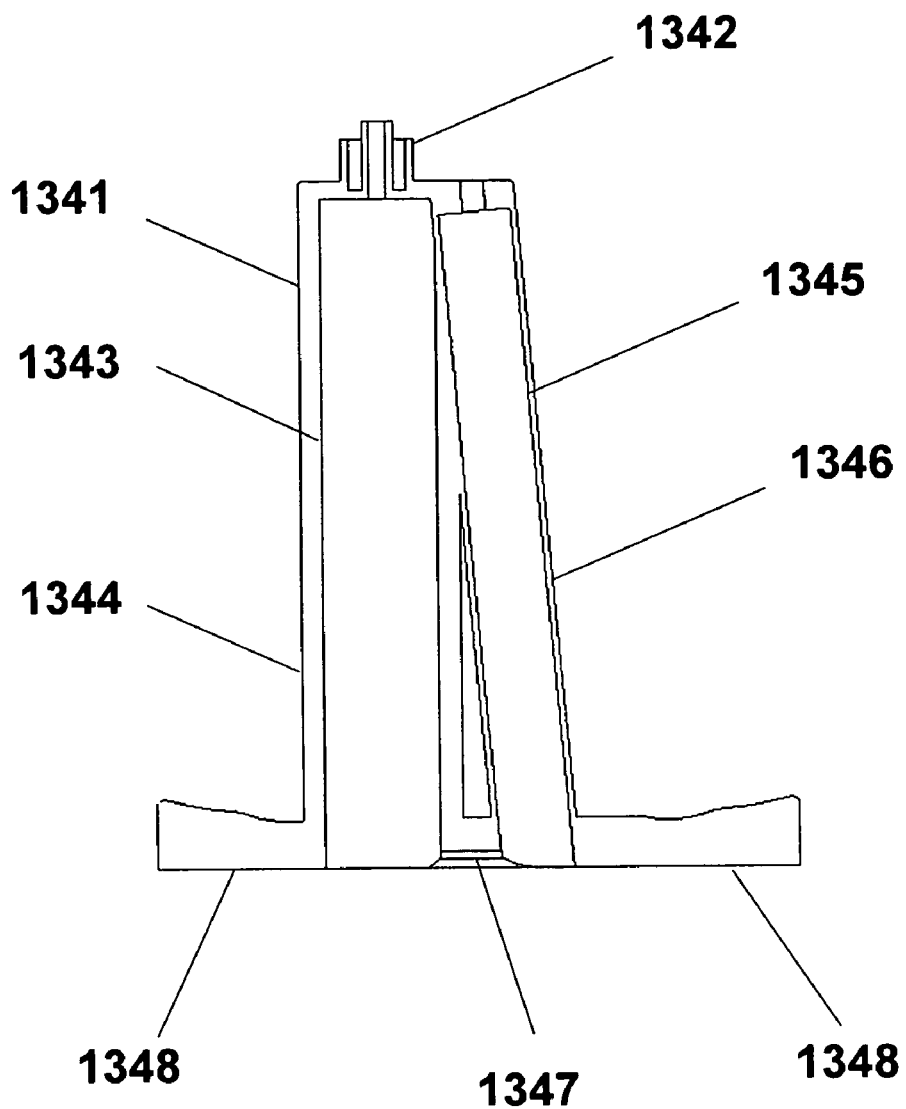

FIG. 13c illustrates a one piece barrel complex that has integrated dominant and accessory barrels. The one-piece barrel complex has integrated dominant and accessory barrels 1341, a syringe needle fitting 1342, an internal portion of the dominant syringe barrel 1343, an external surface of the dominant barrel 1344, an internal barrel of a non-functional accessory driver syringe 1345, an outer surface of the accessory barrel 1346, a static or dynamic pulley 1347, and finger flanges 1348. The accessory barrel in all of these embodiments can include a needle or catheter fitting (not shown). It would be anticipated that different designs of frames could lock in the conventional barrel(s) to the frame from a parallel insertional direction or a non-parallel direction, depending on the design of the locking or fixing mechanisms.

Example Embodiment

Reciprocating Syringes with Plunger Locks

Plunger locks are used in conventional syringes to prevent unintended injection or loss of fluid contained within a syringe, or alternatively to maintain pressure or vacuum in a syringe. Conventional plunger locks will function on a reciprocating syringe in the same fashion as a conventional syringe. However, the mechanically linked plungers in a reciprocating syringe can provide unique plunger locking opportunities. Conventional plunger locks are generally one of (1) a rigid spacer device that fits between the thumb rest of the plunger and the syringe barrel (usually fixes the plunger so that it cannot be depressed), (2) a holder that mechanically binds both the syringe barrel and plunger in a fixed position (prevents both depression and extraction of the plunger), and (3) locking plunger, were there is a fitting on the plunger or barrel that when the plunger is rotated or the fitting is actuated the plunger binds and locks to the barrel. In a conventional syringe, all of these locking devices function on the dominant plunger, as there is no accessory plunger.

In a reciprocating syringe, since the dominant plunger is mechanically bound to the accessory plunger or plunger device, control of the accessory plunger will control the dominant plunger. Thus, the reciprocating syringe is unique in that the locking mechanisms can be applied specifically to the accessory plunger or plunger equivalent instead of the dominant plunger. Accordingly, existing plunger lock mechanisms can be applied to the accessory plunger to control the dominant plunger.

A significant use of reciprocating syringes is to generate vacuum for various procedures. When generating vacuum with a reciprocating syringe, the accessory plunger is depressed with the thumb, resulting in aspiration by the dominant plunger. As the accessory plunger is depressed during aspiration, the thumb rest of the accessory plunger becomes closer to the barrel complex, including the finger flanges, providing a unique opportunity for creating a locking mechanism. In this construct, a locking mechanism can be placed on the accessory plunger close to the thumb rest so that as the thumb rest approaches the syringe barrel complex, the locking mechanism on the plunger interdigitates with the corresponding mechanism on the barrel complex resulting in locking of the accessory plunger to the barrel complex. Since the dominant plunger is mechanically linked to the accessory plunger in a reciprocating fashion, fixing the accessory plunger to the barrel complex fixes the dominant plunger in the aspiration mode, creating a constant vacuum. This can be particularly useful for fine needle aspiration biopsy.

Mechanisms for accomplishing this locking of the accessory plunger to the barrel complex include mechanical clamps which clamp to the plunger and clamp to barrel complex, by hooks, rings, grommets, compressive mechanisms or other similar devices, male and female connectors (or other complementary connectors) connected to each other by pushing the male and female connectors together and reversibly releasing them, and locking mechanisms on the barrel complex and plunger that actuate by rotating the accessory plunger.

A particularly advantageous method for creating a locking accessory plunger or plunger with the reciprocating syringe takes advantage of the asymmetrical thumb rest and the ability of the reciprocating syringe to have a directionality to the plunger, yet still be able to rotate. Directionality of the plunger in a reciprocating syringe occurs because the pulley is bonded to plunger in one point, and when there is tension on the drive line, the bond point orients towards the pulley, and this places the asymmetrical thumb rest in a predictable position. A locking mechanism that takes advantage of this is shown in FIG. 6.

Figures 6A, 6B:
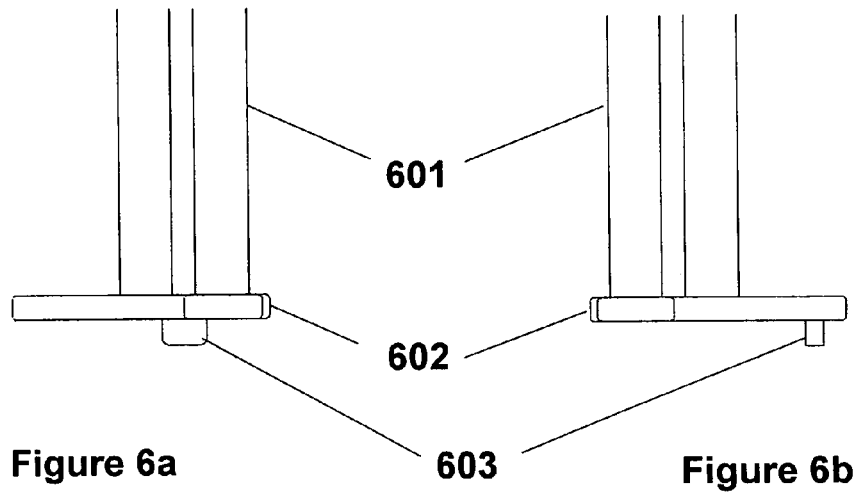
FIG. 6 is a schematic illustration of a locking plunger feature according to the present invention.
Figures 6C, 6D:
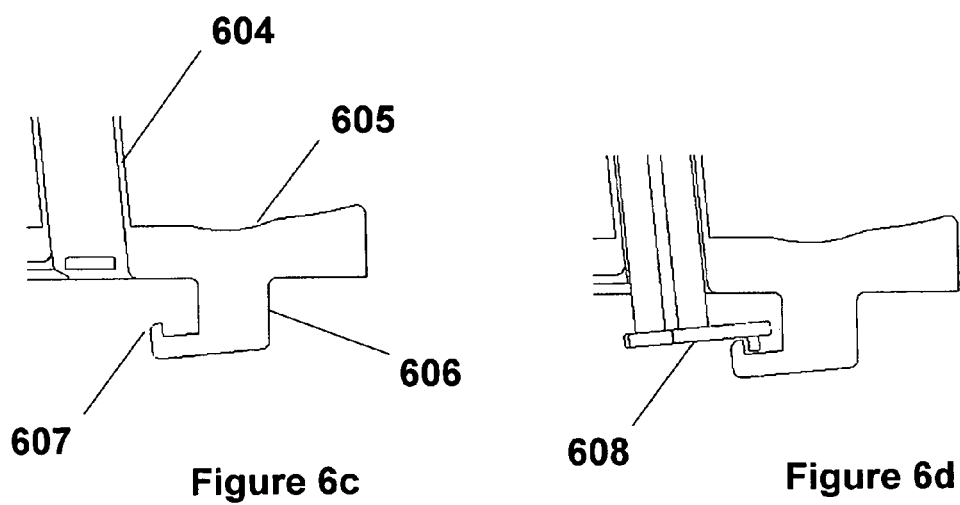
Figure 6E:
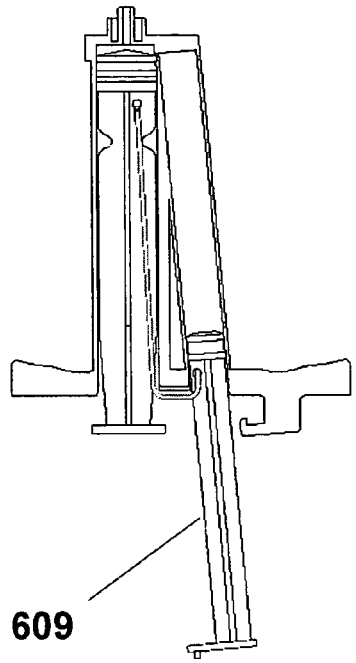
Figure 6F:
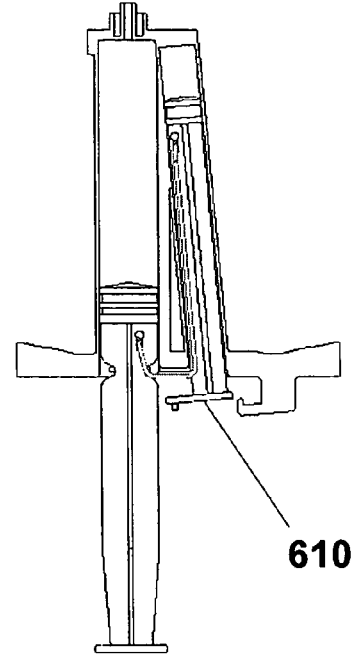
Figure 6G:
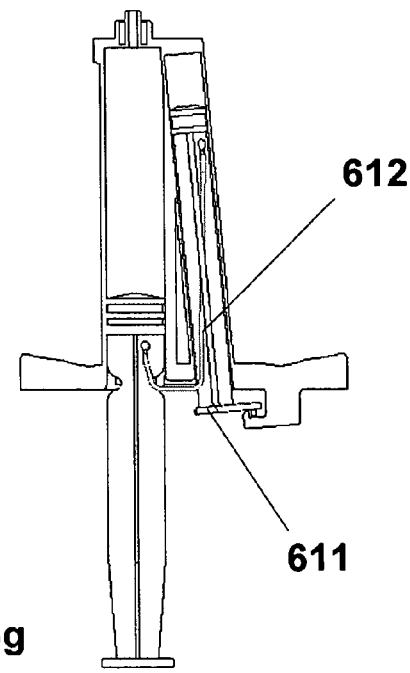

The thumb rest 602 is asymmetric (front view in FIG. 6*a*, side view in FIG. 6*b*) and is attached to the plunger body 601, and may have a retaining bump or protrusion 603 or texture to the surface so that it is retained in the locking mechanism, although this is not required for function. The locking mechanism 606 is shown in side view in FIG. 6*c*. The locking mechanism 606 is integrated with or mounted on the finger flange 605 which is contiguous with the barrel or track wall 604. The locking mechanism 606 has a roof and a space to accommodate the asymmetric thumb rest and may have a retaining edge 607 which interdigitates with the retaining bump or protrusion. When the asymmetrical thumb rest and plunger are rotated (FIG. 6*d*), the thumb rest 608 is locked into the locking mechanism on the finger flange 605. FIG. 6*e* illustrates the reciprocating syringe prior to aspirating, with the accessory plunger 609 fully extended. FIG. 6*f* illustrates a side view of a reciprocating syringe with the accessory plunger depressed 610 and the syringe in full aspiration (vacuum) mode. FIG. 6*g* illustrates a side view of a reciprocating syringe with the asymmetrical thumb rest rotated and locked 611 into the locking fitting on finger flange with drive line rotated 612. There is stored energy in the rotated drive line, so that with easy thumb pressure, the accessory plunger spontaneously rotates, returns to neutral position, and the accessory plunger can be extended, releasing the vacuum.

Example Embodiment

Reciprocating Syringes as Introducers for Wires and Catheters

Often a needle is used as an introducer for placing either a wire or a catheter. However, placing the needle in the correct location without vacuum can be difficult, particularly for low pressure collections of fluid such as in a vein. Since the reciprocating syringe is a one handed syringe, it is ideal for medical procedures where vacuum is desirable while placing vascular or visceral wires and catheters. Reciprocating versions of currently available introducer syringes can be produced as in the examples described elsewhere herein.

Figure 14:
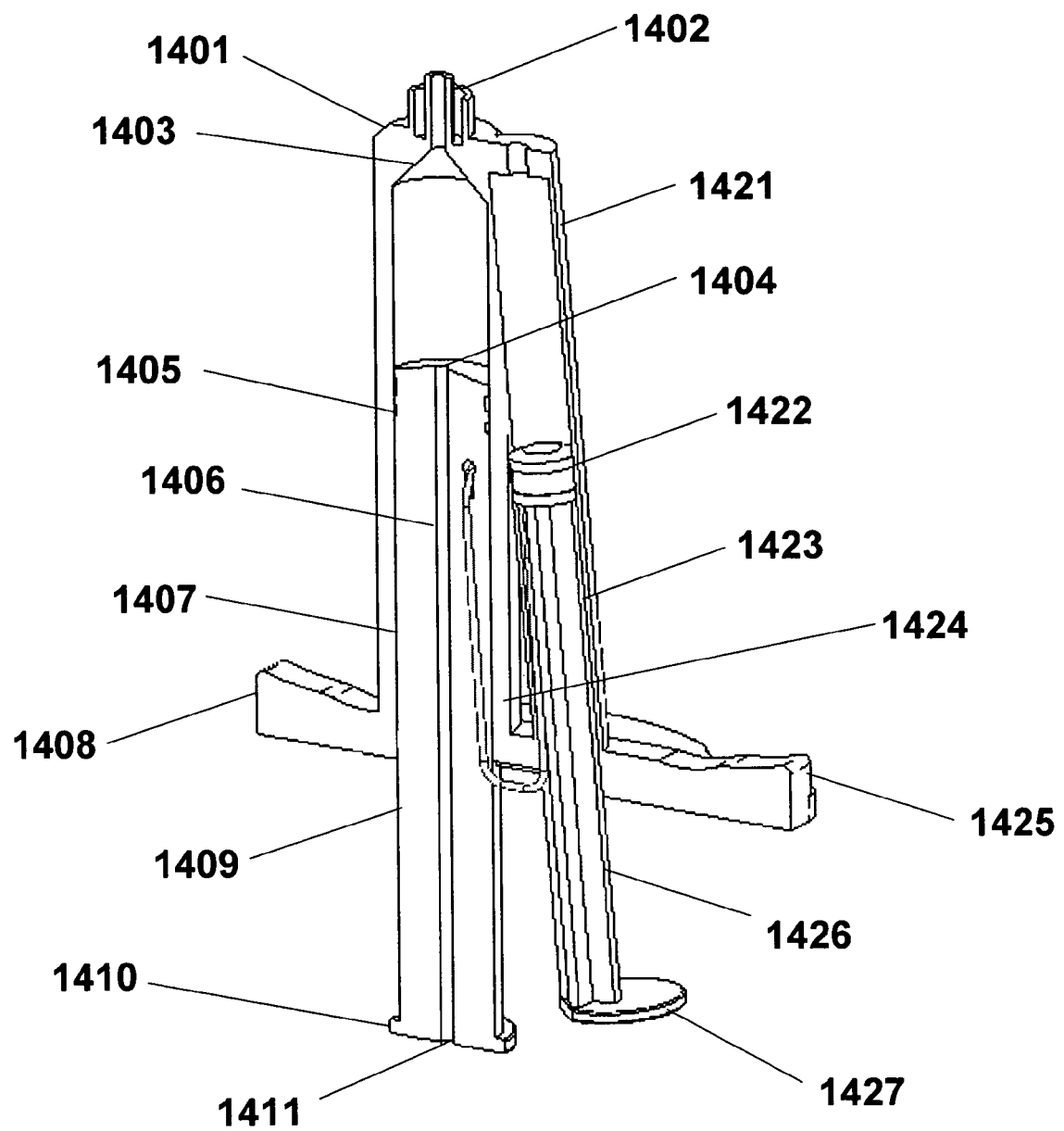
FIG. 14 is a schematic illustration of a reciprocating introducer syringe according to the present invention.

An example of the conversion of a conventional procedure syringe into a reciprocating procedure syringe, in this case, the construction of a reciprocating introducer syringe, is shown in FIG. 14. A conventional introducer syringe is converted to a reciprocating safety syringe by addition of an accessory barrel or track, and the accessory plunger with drive line. In this embodiment, a conventional introducer syringe is introduced to a frame as the dominant syringe 1401. This includes the needle fitting on the introducer syringe 1402; female introducer fitting with funnel-shaped surface and angled barrel to permit threading of wire 1403 (other introducer mechanisms can also be used in an analogous fashion); exit lumen in the plunger for an introducer wire, with an optional septum or valve to prevent movement of gas or liquid 1404. The reciprocating syringe further comprises a stopper/drag device 1405 on the plunger of the dominant safety syringe with or without septum or valve to prevent movement of gas or liquid; an introducer wire lumen 1406 in barrel shaft; a functional barrel 1407 of the introducer syringe; finger flange 1408; the functional plunger 1409; symmetrical or asymmetric thumb rest 1410; entrance lumen in plunger for introducer wire 1411, with an optional septum or valve to prevent movement of gas or liquid through the lumen; accessory barrel or track 1421 with or without needle fitting; stopper/drag device 1422 on an accessory plunger; barrel or track 1423 for accessory plunger, plunger-equivalent, or reciprocating member; reciprocating mechanical link 1424 between plungers (pulley, gear, hydraulics, or mechanism) in this case a monofilament pulley mechanism which is attached to both plungers; finger flange 1425; accessory plunger 1426, plunger equivalent, or reciprocating member, symmetrical or asymmetric thumb test 1427 on accessory plunger. Any introducer syringe can similarly be converted into a reciprocating introducer syringe. Alternatively, as in any reciprocating syringe, the entire introducer syringe barrel complex can be manufactured in one piece or several pieces and assembled.

Figures 7A, 7B:
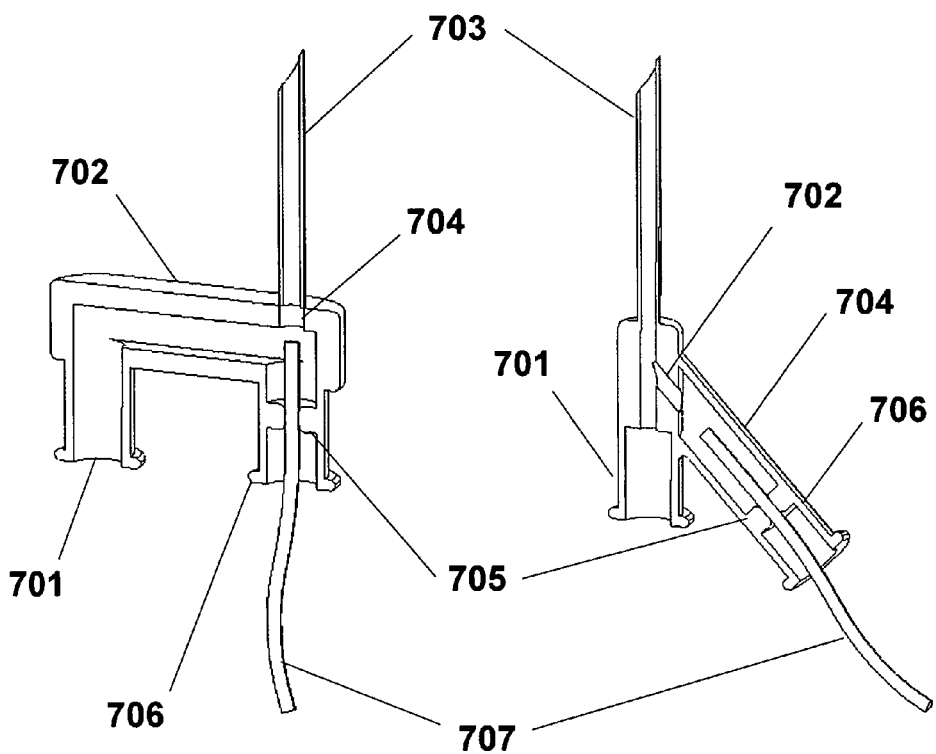
FIG. 7 is a schematic illustration of an internal introducer fitting according to the present invention suitable for wires and catheters.

Alternatively, a reciprocating syringe can be transformed into an introducer syringe with the proper needle fitting. Examples of such internal introducer fittings are shown in FIG. 7(*a,b*). FIG. 7*a* is a side view of a straight shot reciprocating introducer. FIG. 7*b* is a side view of a side access reciprocating introducer. For both versions, there must be a fitting for the reciprocating syringe 701, a connection of the fitting to an introducer needle 702 so that vacuum can be applied to the introducer needle, an introducer needle 703; an introducer port 704 to allow the line or wire to be threaded up the introducer needle, an optional airtight membrane, annular seal, leaflet, funnel or other seal 705 to prevent loss of vacuum (alternatively, this can be replaced with a plug which would fit in the introducer fitting), an introducer fitting 706 to allow access to the introducer needle, and a wire or catheter 707 which is threaded into the introducer needle. These introducer fittings could take a variety of other forms as well, but basically vacuum is applied by the reciprocating syringe until there is blood or fluid return, and then the wire or line is thread up the introducer port.

Most angiocath needles have an external catheter that is threaded over an introducer needle. Most of these needles now are safety versions, and internalize the introducer needle after use. However, since the reciprocating syringe is a one-handed stable syringe, it can be used as an introducer source of vacuum, with a needle introducer mounted on the syringe. Once vascular access is obtained, then the catheter can be pushed over the needle into the vein or body cavity as is completely conventional. The plunger lock version of this syringe can also be valuable for this use. Safety versions of the reciprocating syringe can then accommodate the introducer needle.

Example Embodiment

Reciprocating Safety Syringes

Figure 8:
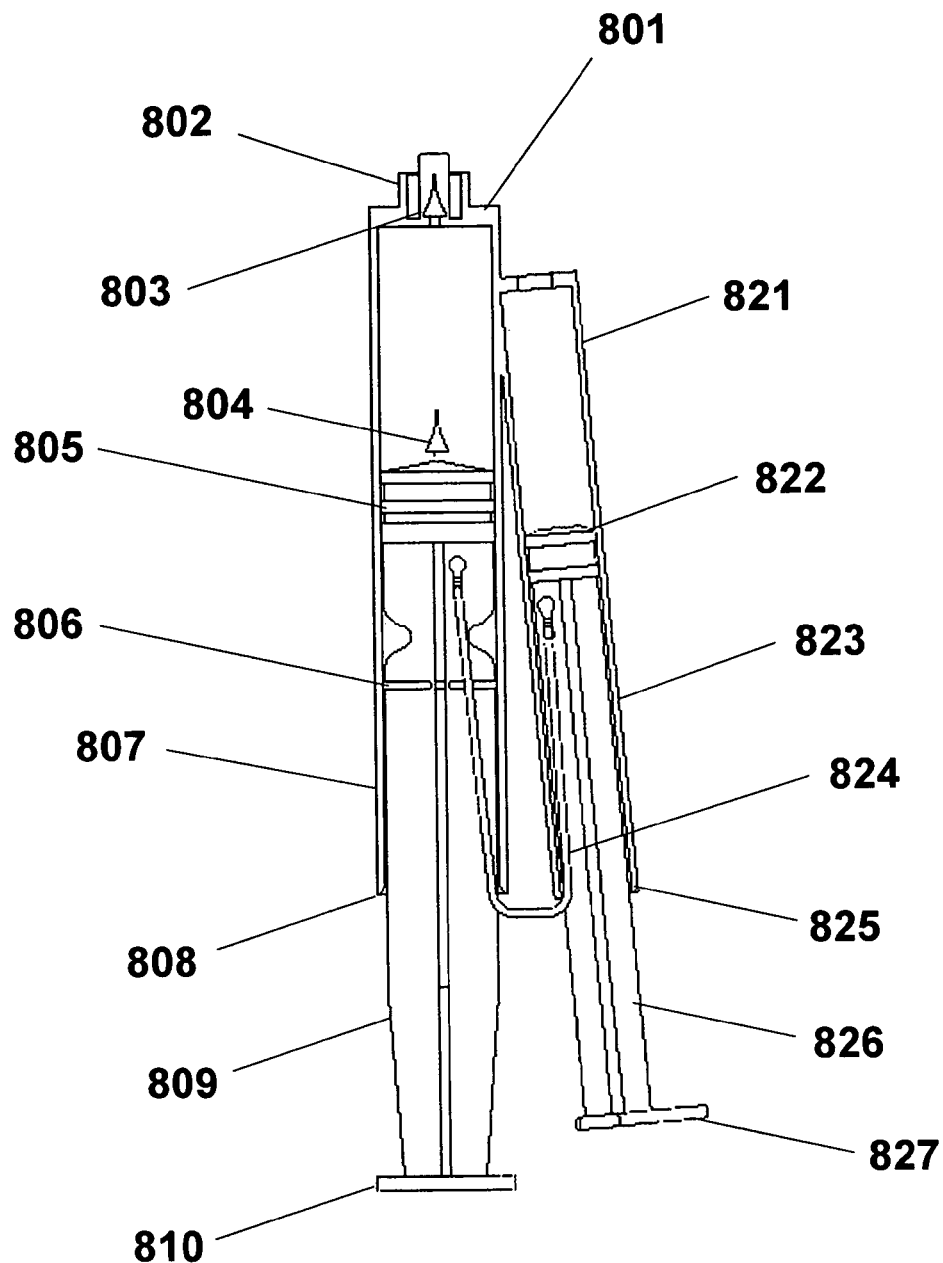
FIG. 8 is a schematic illustration of a reciprocating safety syringe according to the present invention.

Reciprocating versions of safety syringes can be produced using a frame-based approach as described elsewhere herein. An example of the construction of a reciprocating safety syringe is shown in FIG. 8, where a conventional safety syringe is converted to a reciprocating safety syringe by addition of an accessory barrel or track, and the accessory plunger with drive line. In this example embodiment, a conventional safety syringe is introduced as the dominant syringe 801. This includes a needle fitting on the safety syringe 802; female safety fitting with needle fitting housing 803 although other safety mechanism can also be used; male safety fitting on the plunger 804. FIG. 8 illustrates a stopper/drag device 805 on the plunger of the dominant safety syringe; a snap off device in the plunger to prevent reuse 806; the functional barrel of the safety syringe 807; finger flange 808; functional plunger 809; symmetrical or asymmetric thumb rest 810; accessory barrel or track 821 with or without needle fitting; a stopper/drag device 822 on an accessory plunger; a barrel or track 823 for the accessory plunger, plunger-equivalent, or reciprocating member; a reciprocating mechanical link 824 between plungers (pulley, gear, hydraulics, or mechanism) in the example a monofilament pulley mechanism which is attached to both plungers; finger flange 825; accessory plunger 826, plunger equivalent, or reciprocating member, and symmetrical or asymmetric thumb rest 827 on accessory plunger.

Figure 9:
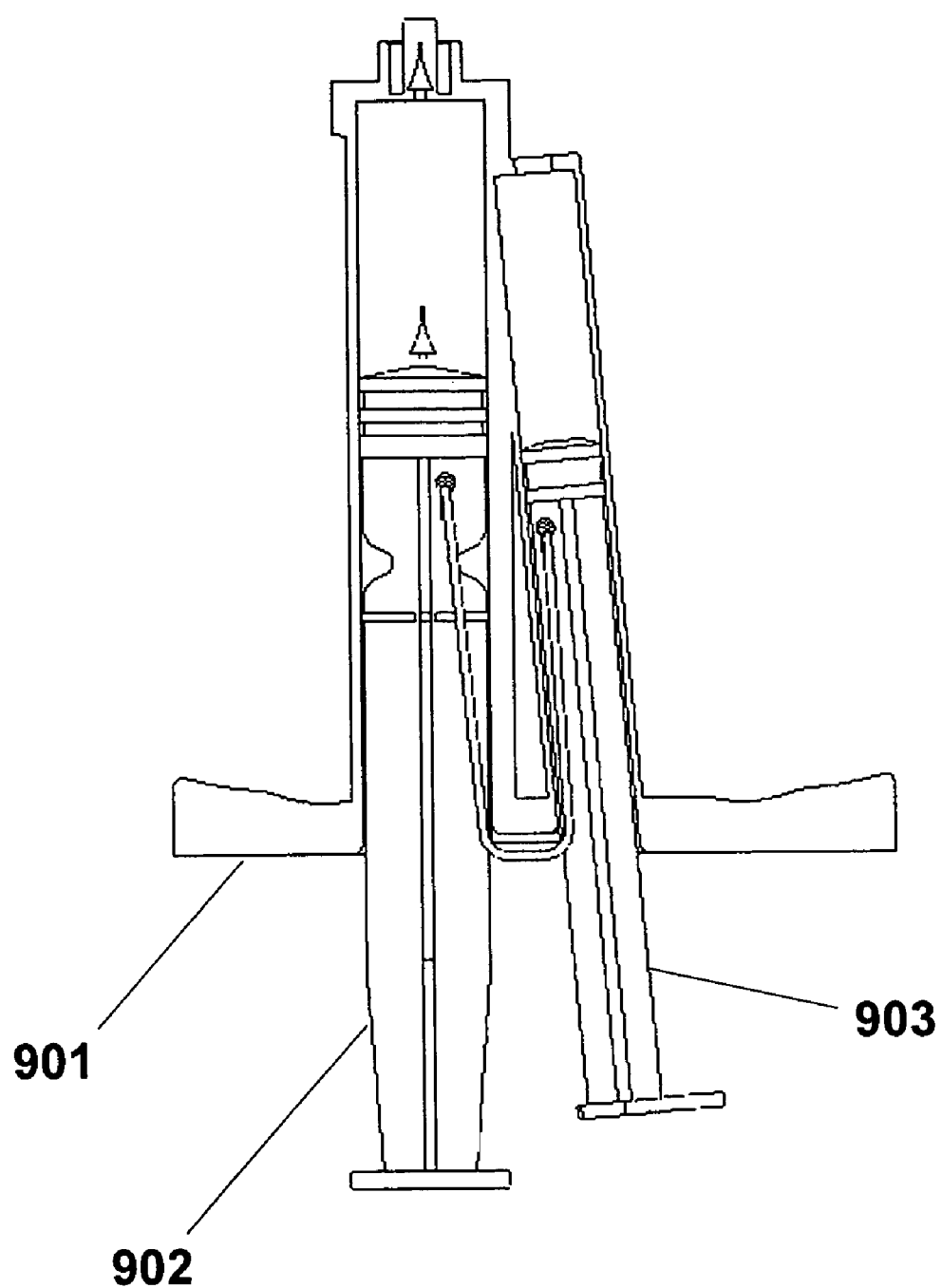
FIG. 9 is a schematic illustration of a reciprocating safety syringe according to the present invention.

FIG. 9 illustrates the assembled reciprocating safety syringe: housing 901 or frame that creates the barrel complex; conventional safety syringe and plunger 902; and accessory plunger 903 and accessory barrel or track.

Example Embodiment

Reciprocating Menghini Needle Syringe

Menghini needle syringes are biopsy needles where the needle is integrated with the syringe and the stylet of the needle is actually integrated into the plunger of the syringe. See, e.g., U.S. Pat. No. 4,619,272. Existing and future Menghini needle syringes can be constructed using frame-based methods as described elsewhere herein.

Figure 10:
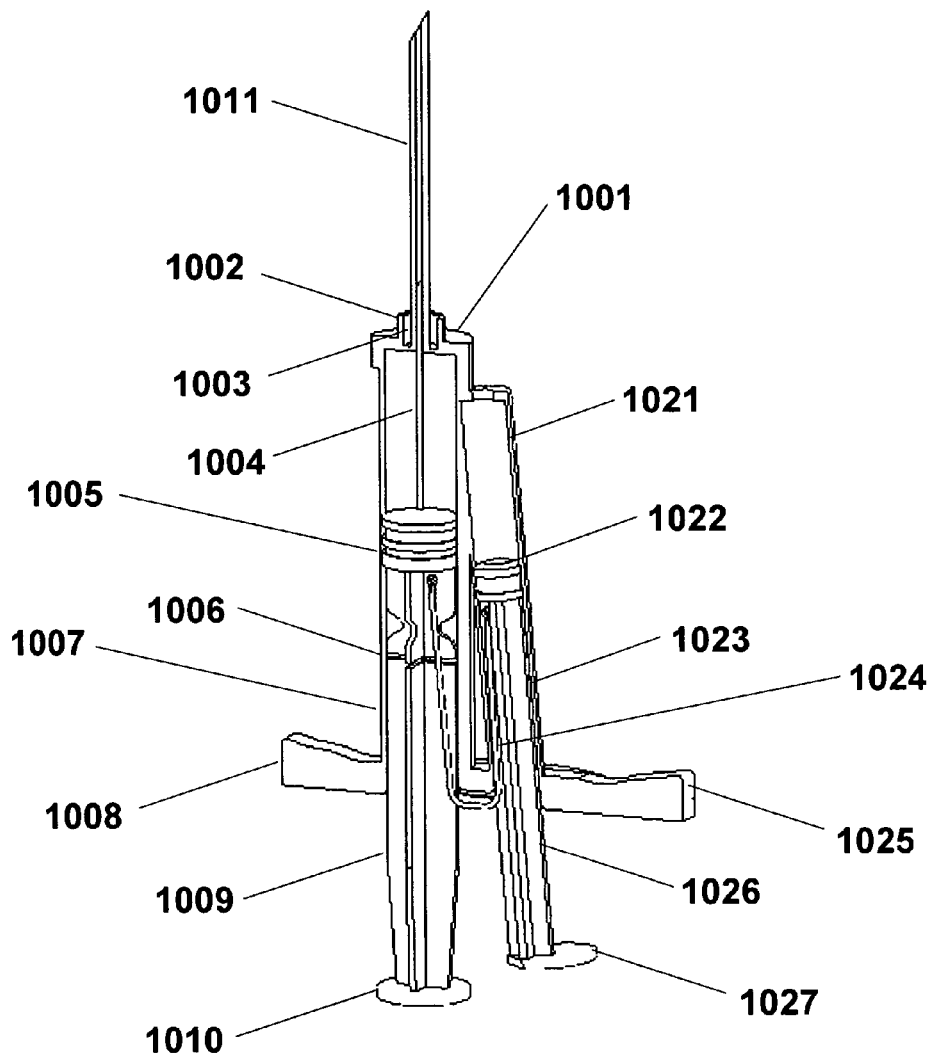
FIG. 10 is a schematic illustration of a reciprocating Menghini needle syringe according to the present invention.

An example of the construction of a reciprocating Menghini syringe is shown in FIG. 10, where a conventional Menghini needle syringe is converted to a reciprocating Menghini needle syringe by addition of an accessory barrel or track, and an accessory plunger with drive line. In this example embodiment, a conventional Menghini needle syringe is introduced as the dominant syringe 1001. This includes the needle fitting on Menghini needle syringe 1002; track for the Menghini needle stylet within the needle fitting housing 1003 (other track mechanisms can also be used); Menghini needle stylet on the plunger 1004. The syringe further comprises a stopper/drag device 1005 on the plunger of the dominant Menghini needle syringe; a snap off or locking device 1006 in the plunger to prevent reuse or to lock the plunger in position; the functional barrel of Menghini needle syringe 1007; finger flange 1008; functional plunger 1009; symmetrical or asymmetric thumb rest 1010; biopsy needle portion of the Menghini needle syringe 1011; accessory barrel or track 1021 with or without needle fitting; a stopper/drag device 1022 on an accessory plunger; a barrel or track 1023 for an accessory plunger, plunger-equivalent, or reciprocating member; a reciprocating mechanical link 1024 between plungers (pulley, gear, hydraulics, or mechanism) in this case a monofilament pulley mechanism which is attached to both plungers; finger flange 1025; accessory plunger 1026, plunger equivalent, or reciprocating member, and symmetrical or asymmetric thumb rest 1027 on the accessory plunger. All of the barrel complexes described above can be utilized for the reciprocating Menghini needle syringe.

Example Embodiment

Double Reciprocating Syringe

Figure 11:
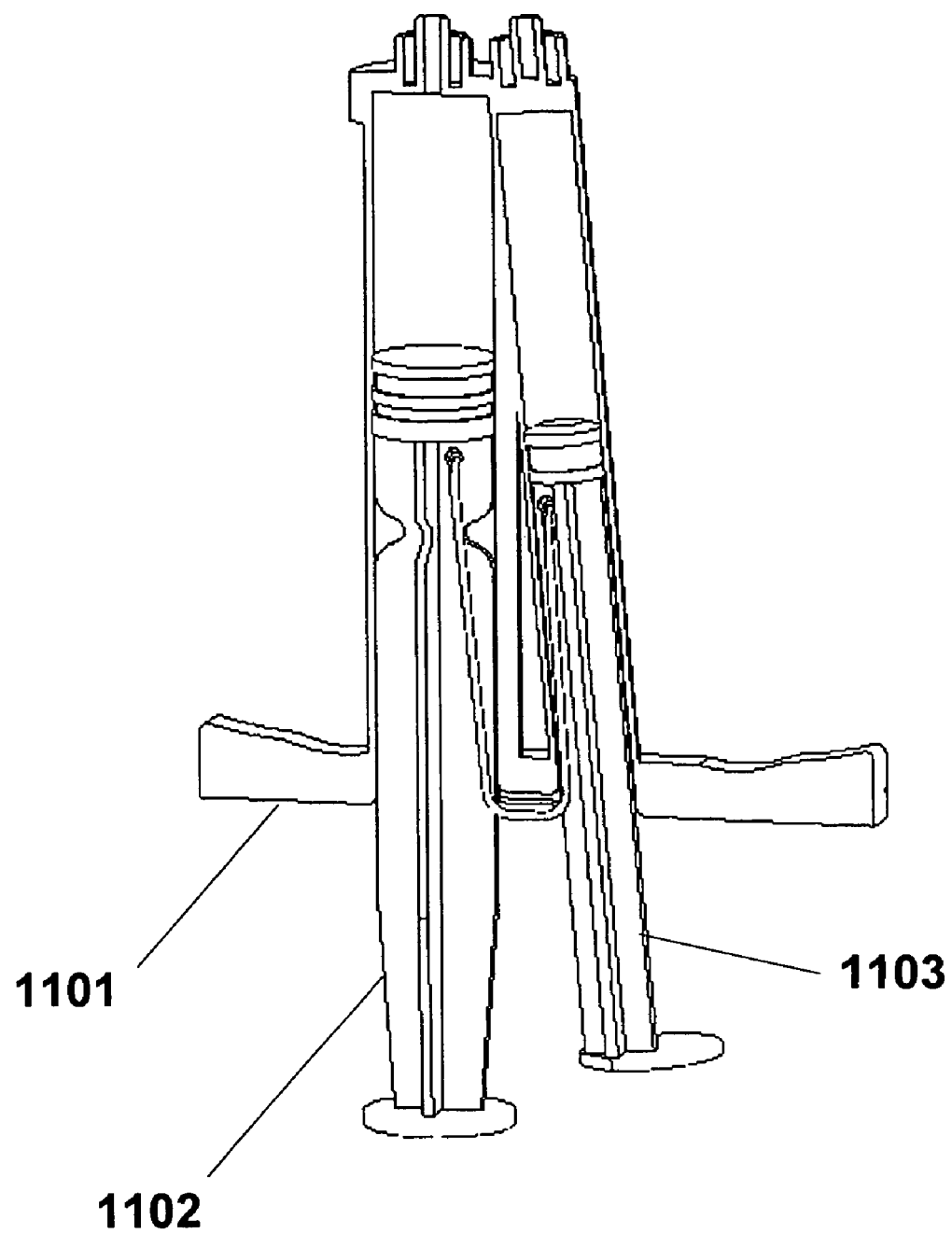
FIG. 11 is a schematic illustration of a reciprocating syringe according to the present invention, with two functional barrels and needle catheter fittings.

In certain applications, a reciprocating syringe with two functional syringes can be advantageous. Example applications include those where something needs to be aspirated and another component needs to be injected, or in certain double cycle hand-held piston pumps. Using frame-based methods, double reciprocating versions of every existing and future syringe can be constructed. FIG. 11 illustrates two functional syringes and barrels joined in a reciprocating fashion. A housing or frame 1101 creates the barrel complex; a first conventional syringe and plunger with a needle or catheter fitting 1102 mounts with the frame; a second conventional plunger and barrel with a needle or catheter fitting 1103 mounts with the frame. The syringes can be identical in volume, but need not. Either or both of the syringes can be specialty syringes.

Example Embodiment

High Pressure Reciprocating Syringe

Figure 12:
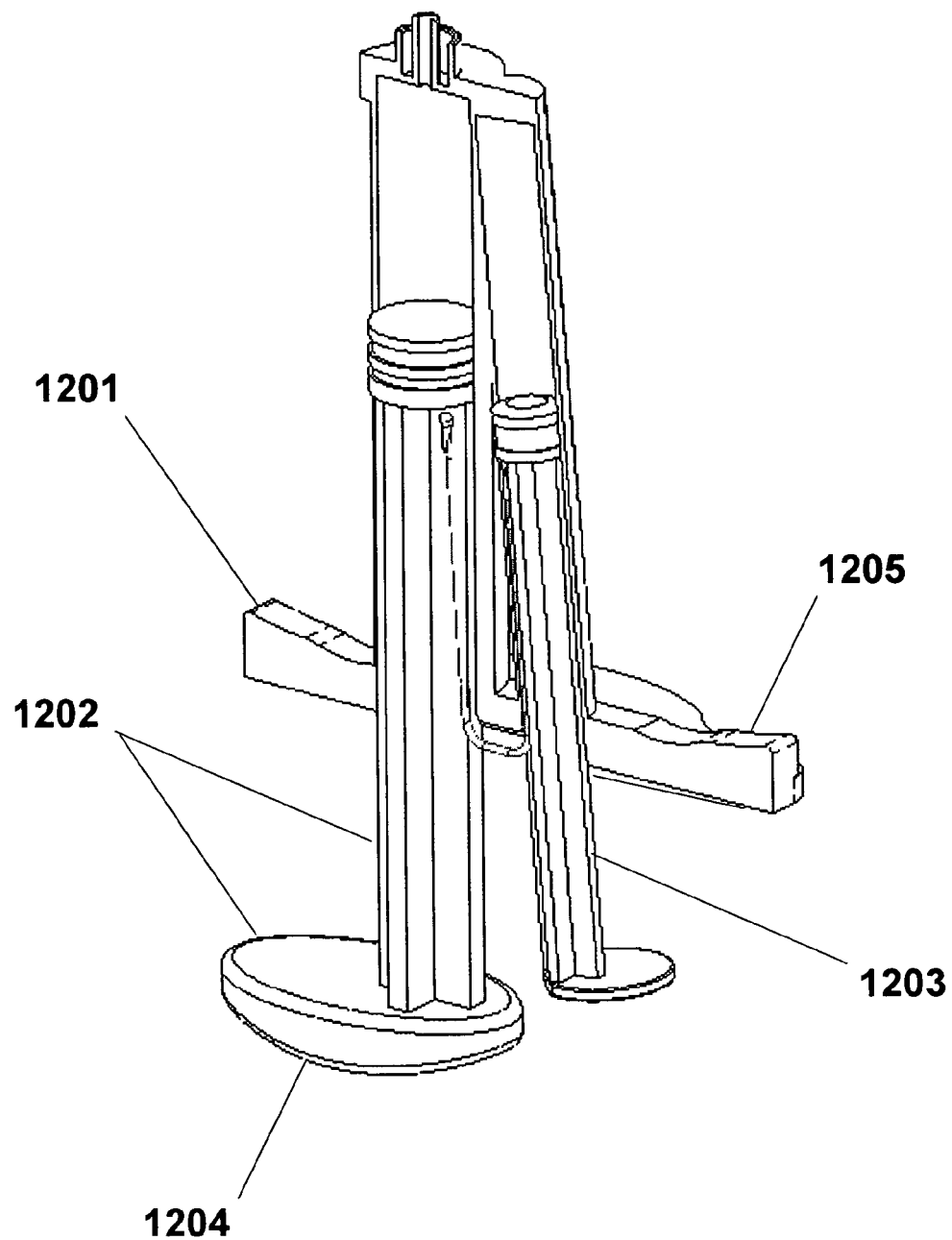
FIG. 12 is a schematic illustration of a high pressure reciprocating syringe according to the present invention, suitable for use with contrast and other rapid high pressure injections.

In certain applications, a reciprocating syringe with high pressure capabilities can be advantageous, for example for rapid injection of contrast for angiographic and other radiologic and imaging procedures. Using frame-based methods, reciprocating versions of every high pressure syringe can be constructed. FIG. 12 illustrates an example of a high pressure syringe for rapid, high pressure injections, with a high pressure functional syringe and an appropriately modified plunger. A housing or frame or integrated barrel complex creates the barrel complex 1201; a high pressure barrel and plunger 1202 mount with the frame; an accessory barrel and plunger 1203 mount with the frame. The plunger can have appropriately configured thumb rest 1204 and finger flanges 1205.

The particular sizes and equipment discussed above are cited merely to illustrate particular embodiments of the invention. It is contemplated that the use of the invention may involve components having different sizes and characteristics. It is intended that the scope of the invention be defined by the claims appended hereto.

What is claimed is:

1. A reciprocating syringe, comprising:
a) an external frame, defining a first receptacle suitable for retaining a first insertable syringe barrel in a relationship with the frame that discourages translation of the first insertable syringe barrel relative to the frame;
b) a first plunger suitable for use with a syringe barrel retained in the first receptacle;
c) an auxiliary actuator slidably mounted with the frame and suitable for manual actuation by a human hand;
d) wherein the auxiliary actuator is coupled with the first plunger such that motion of the first plunger in a direction into a syringe barrel retained in the first receptacle causes motion of the auxiliary actuator in an actuation direction along an actuation axis, and such that motion of the auxiliary actuator along the actuation axis opposite the actuation direction causes motion of the first plunger in a direction out of a syringe barrel retained in the first receptacle, wherein the plunger is configured to accept force directly from a human hand to control the motion of the plunger in a syringe barrel retained in the first receptacle, and wherein the frame and the first plunger do not form a syringe when there is not a syringe barrel retained in the first receptacle.

2. A reciprocating syringe as in claim 1, wherein the first plunger and the auxiliary actuator are connected by a line, and wherein the frame defines a pulley situated such that the line passes over the pulley when the first plunger engages the retained first insertable syringe barrel.

3. A reciprocating syringe as in claim 2, wherein the pulley comprises a surface over which the line passes.

4. A reciprocating syringe as in claim 3, wherein the surface defines a path length for the line across the surface dependent on the path the line takes across the surface, and such that the range of possible path lengths smoothly increases as the line moves farther from the path defining the shortest path length.

5. A reciprocating syringe as in claim 4, wherein the surface further defines a groove in the surface, where the path through the groove is the shortest path length, which groove is adapted to allow slidable engagement with the line when the first plunger is moved in a direction into the retained first insertable syringe barrel or the auxiliary actuator is moved in a direction opposite the actuation direction.

6. A reciprocating syringe as in claim 3, wherein the pulley comprises a groove in the surface, which groove is adapted to allow slidable engagement with the line when the first plunger is moved in a direction into the retained first insertable syringe barrel or the auxiliary actuator is moved in a direction opposite the actuation direction.

7. A reciprocating syringe as in claim 1, wherein the external frame is configured such that a syringe barrel retained in the first receptacle defines a first axis along the direction of motion of the first plunger when engaged with such syringe barrel, and wherein the first axis is not parallel to the actuation direction.

8. A reciprocating syringe as in claim 7, wherein the separation between the first axis and the actuation direction is less near the portion of the external frame near where the needle end of a syringe barrel is retained in the first receptacle than near the portion of the external frame near where the plunger end of such syringe barrel is retained in the first receptacle.

9. A reciprocating syringe as in claim 1, wherein the frame defines an optically transmissive portion located relative to the first receptacle such that markings on the retained first insertable syringe barrel can be seen through the optically transmissive portion.

10. A reciprocating syringe as in claim 9, wherein the optically transmissive portion comprises an open portion of the frame, or an optically clear window in the frame.

11. A reciprocating syringe as in claim 1, wherein the first plunger is shaped to engage a locking mechanism of the frame, wherein the locking mechanism substantially prevents motion of the first plunger in at least one of (a) inwards relative to the retained first insertable syringe barrel, and (b) outwards relative to the retained first insertable syringe barrel, when engaged.

12. A reciprocating syringe as in claim 1, wherein the auxiliary actuator is shaped to engage a locking mechanism of the frame, wherein the locking mechanism substantially prevents motion of the auxiliary actuator in at least one of (a) the actuation direction, and (b) opposite the actuation direction, when engaged.

13. A reciprocating syringe as in claim 1, further comprising a first retained insertable syringe barrel, wherein the retained first insertable syringe barrel is a barrel of an introducer syringe, and wherein the first plunger has an exit lumen suitable for passage of an introducer wire therethrough.

14. A reciprocating syringe, comprising:
a) an external frame, defining a first receptacle suitable for retaining a first insertable syringe barrel in a relationship with the frame that discourages translation of the first insertable syringe barrel relative to the frame, and defining a second receptacle suitable for retaining a second insertable syringe barrel in a relationship with the frame that discourages translation of the second insertable syringe barrel relative to the frame;
b) a plunger complex, comprising a first plunger suitable for use with a syringe barrel retained in the first receptacle, and a second plunger suitable for use with a syringe barrel retained in the second receptacle, wherein the first and second plungers are coupled such that motion of the first plunger in a direction into a syringe barrel retained in the first receptacle causes motion of the second plunger in a direction out of a syringe barrel retained in the second receptacle, and such that motion of the second plunger in a direction into a syringe barrel retained in the second receptacle causes motion of the first plunger in a direction out of a syringe barrel retained in the first receptacle; wherein the plunger complex and the external frame do not form a sealed syringe when there is no syringe barrel in either of the first and second receptacle, and
c) wherein the external frame is configured to allow force by a human hand directed into a syringe barrel retained in the first receptacle to be applied to the first plunger, and to allow force by a human hand directed into a syringe barrel retained in the second receptacle to be applied to the second plunger, wherein the hand directly applies forces to said plungers.

15. A reciprocating syringe as in claim 14, wherein the first and second plungers are connected by a line, and wherein the frame defines a pulley situated such that the line passes over the pulley when the first plunger engages the retained first insertable syringe barrel and the second plunger engages the retained second insertable syringe barrel.

16. A reciprocating syringe as in claim 15, wherein the pulley comprises a surface over which the line passes.

17. A reciprocating syringe as in claim 16, wherein the pulley comprises a groove in the surface, which groove is adapted to allow slidable engagement with the line when either plunger is moved in a direction into the corresponding retained insertable syringe barrel.

18. A reciprocating syringe as in claim 14, wherein the frame defines an optically transmissive portion located relative to the first receptacle such that markings on a syringe barrel retained in the first receptacle can be seen through the optically transmissive portion.

19. A reciprocating syringe as in claim 18, wherein the optically transmissive portion comprises an open portion of the frame, or an optically clear window in the frame.

20. A reciprocating syringe as in claim 18, wherein the frame defines a second optically transmissive portion located relative to the second receptacle such that markings on a syringe barrel retained in the second receptacle can be seen through the second optically transmissive portion.

21. A reciprocating syringe as in claim 14, wherein the first plunger is shaped to engage a locking mechanism of the frame, wherein the locking mechanism substantially prevents motion of the first plunger in at least one of (a) inwards relative to a syringe barrel retained in the first receptacle, and (b) outwards relative to a syringe barrel retained in the first receptacle, when engaged.

22. A reciprocating syringe as in claim 14, further comprising a first insertable syringe barrel, wherein the retained first insertable syringe barrel is a barrel of an introducer syringe, and wherein the first plunger has an exit lumen suitable for passage of an introducer wire therethrough.

23. A reciprocating syringe, comprising:
a) an external frame, defining a first receptacle suitable for retaining a first insertable syringe barrel in a relationship with the frame that discourages translation of the first insertable syringe barrel relative to the frame, and defining a second receptacle suitable for retaining a second insertable syringe barrel in a relationship with the frame that discourages translation of the second insertable syringe barrel relative to the frame;
b) a plunger complex, comprising a first plunger suitable for use with a syringe barrel retained in the first receptacle, and a second plunger suitable for use with a syringe barrel retained in the second receptacle, wherein the first and second plungers are coupled such that motion of the first plunger in a direction into a syringe barrel retained in the first receptacle causes motion of the second plunger in a direction out of a syringe barrel retained in the second receptacle, and such that motion of the second plunger in a direction into a syringe barrel retained in the second receptacle causes motion of the first plunger in a direction out of a syringe barrel retained in the first receptacle; wherein the plunger complex and the external frame do not form a sealed syringe when there is no syringe barrel in either of the first and second receptacles;
c) wherein the first and second plungers are connected by a line, and wherein the frame defines a pulley situated such that the line passes over the pulley when the first plunger engages the retained first insertable syringe barrel and the second plunger engages the retained second insertable syringe barrel;
d) wherein the pulley comprises a surface over which the line passes and wherein the pulley comprises a groove in the surface, which groove is adapted to allow slidable engagement with the line when either plunger is moved in a direction into the corresponding retained insertable syringe barrel; and
e) wherein the surface defines a path length for the line across the surface dependent on the path the line takes across the surface, and such that the range of the possible path lengths smoothly increases as the line moves farther from the path defining the shortest path length.

24. A reciprocating syringe as in claim 23, wherein the surface further defines a groove in the surface, where the path through the groove is the shortest path length, which groove is adapted to allow slidable engagement with the line when either plunger is moved in a direction into the corresponding retained insertable syringe barrel.

25. A reciprocating syringe, comprising:
a) an external frame, defining a first receptacle suitable for retaining a first insertable syringe barrel in a relationship with the frame that discourages translation of the first insertable syringe barrel relative to the frame, and defining a second receptacle suitable for retaining a second insertable syringe barrel in a relationship with the frame that discourages translation of the second insertable syringe barrel relative to the frame;
b) a plunger complex, comprising a first plunger suitable for use with a syringe barrel retained in the first receptacle, and a second plunger suitable for use with a syringe barrel retained in the second receptacle, wherein the first and second plungers are coupled such that motion of the first plunger in a direction into a syringe barrel retained in the first receptacle causes motion of the second plunger in a direction out of a syringe barrel retained in the second receptacle, and such that motion of the second plunger in a direction into a syringe barrel retained in the second receptacle causes motion of the first plunger in a direction out of a syringe barrel retained in the first receptacle; wherein the plunger complex and the external frame do not form a sealed syringe when there is no syringe barrel in either of the first and second receptacles,
c) wherein the external frame is configured such that a syringe barrel retained in the first receptacle defines a first axis along the direction of motion of the first plunger when engaged with such syringe barrel, and wherein the external frame is configured such that a syringe barrel retained in the second receptacle defines a second axis along the direction of motion of the second plunger when engaged with such syringe barrel, and wherein the first axis is not parallel to the second axis.

26. A reciprocating syringe as in claim 25, wherein the external frame is configured such that the separation between the first axis and the second axis is less near the region of the frame near where the needle ends of syringe barrels in the first and second receptacles are retained than near the region of the frame where the plunger ends of such syringe barrels are retained.

* * * * *